United States Patent [19]

Carini et al.

[11] Patent Number: 4,880,804
[45] Date of Patent: Nov. 14, 1989

[54] ANGIOTENSIN II RECEPTOR BLOCKING BENZIMIDAZOLES

[75] Inventors: David J. Carini, Wilmington; John Jonas V. Duncia, Newark, both of Del.; Sung-Eun Yoo, Daejeon, Rep. of Korea

[73] Assignee: E. I. Du Pont De Nemours and Company, Wilmington, Del.

[21] Appl. No.: 142,053

[22] Filed: Jan. 7, 1988

[51] Int. Cl.$^4$ .................. A61K 31/535; C07D 233/56
[52] U.S. Cl. .................... 514/234.5; 514/253; 514/322; 514/374; 514/381; 514/394; 544/139; 544/370; 546/199; 548/215; 548/252; 548/253; 548/325; 548/327; 548/330
[58] Field of Search ............... 548/325, 327, 330, 215, 548/252, 253; 544/139, 370; 546/199; 514/234.5, 253, 322, 374, 381, 394

[56] References Cited

U.S. PATENT DOCUMENTS

| | | | |
|---|---|---|---|
| 3,772,315 | 11/1973 | Regel et al. | 546/278 |
| 3,821,393 | 6/1974 | Janiak et al. | 548/325 X |
| 4,207,324 | 6/1980 | Matsamura et al. | 548/336 X |
| 4,226,878 | 10/1980 | Ilzuka et al. | 548/335 X |
| 4,328,349 | 5/1982 | Grayboyes et al. | 548/343 |
| 4,340,598 | 7/1982 | Furukawa et al. | 548/337 X |
| 4,347,364 | 8/1982 | Walser et al. | 546/256 |
| 4,347,365 | 8/1982 | Walser et al. | 546/256 |
| 4,355,040 | 10/1982 | Furukawa et al. | 548/336 X |
| 4,379,927 | 4/1983 | Vorbrüggen | 544/139 |
| 4,448,781 | 5/1984 | Cross et al. | 548/252 X |
| 4,463,011 | 7/1984 | Ogata et al. | 548/336 X |
| 4,612,323 | 9/1986 | Kisida et al. | 548/325 X |
| 4,663,339 | 5/1987 | Kisida et al. | 548/325 X |

FOREIGN PATENT DOCUMENTS

| | | |
|---|---|---|
| 090978 | 10/1983 | European Pat. Off. |
| 103647 | 3/1984 | European Pat. Off. |
| 125033 | 11/1984 | European Pat. Off. |
| 125783 | 11/1984 | European Pat. Off. |
| 146228 | 6/1985 | European Pat. Off. |
| 3426195 | 1/1986 | Fed. Rep. of Germany |
| 3426018 | 1/1988 | Fed. Rep. of Germany |
| 8298270 | 6/1982 | Japan |

OTHER PUBLICATIONS

H. Torii et al., *Takeda Kenkyushoho*, 41, No. 3/4, 180–191 (1982).
D. Pals et al., *Circulation Research*, 29, 673 (1971).
Streeten & Anderson, *Handbook of Hypertension*, vol. 5, Clinical Pharmacology of Antihypertensive Drugs, A. E. Doyl (Ed.), Elsevier Science Publishers, B. V., p. 246 (1984).
Satoh et al., *Circ. Res.*, 36/37 (Suppl. I):1–89, 1975.
M. Blasingham et al., *Am. J. Physiol.*, 239:F60, 1980.
P. Wong et al., *Pharmacol. Exp. Ther.*, 215:104, 1980.
M. Dunn, *Hospital Practice*, 19:-9, 1984.
V. Dzau et al., *N. Eng. J. Med.*, 310:347, 1984.
B. Lindgren et al., *Eur. J. Pharmacol.*, 135:383, 1987.
R. Zatz et al., *Kidney International*, vol. 31, Suppl. 20, pp. S-123 to S-129.
P. Wong et al., *Life Sciences*, vol. 27, pp. 1291–1297 (1980).
M. Schmidt et al., *J. Cardiovascular Pharmacology*, vol. 8, pp. S100–S105 (1986).

Primary Examiner—Richard A. Schwartz

[57] ABSTRACT

Substituted benzimidazoles such as

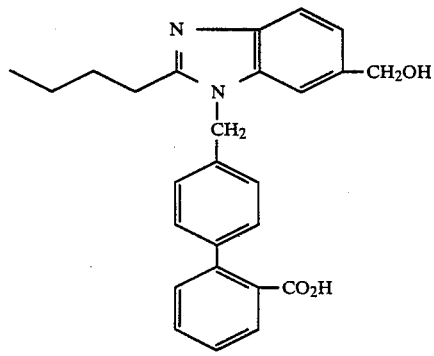

and pharmaceutically suitable salts thereof are useful as angiotensin II blockers. These compounds have activity in treating hypertension and congestive heart failure.

13 Claims, No Drawings

ANGIOTENSIN II RECEPTOR BLOCKING BENZIMIDAZOLES TECHNICAL FIELD

This invention relates to novel substituted benzimidazoles, and processes for their preparation, pharmaceutical compositions containing them and pharmaceutical methods using them.

BACKGROUND OF THE INVENTION

The compounds of this invention inhibit the action of the hormone angiotensin II (AII) and are useful therefore in alleviating angiotensin induced hypertension. The enzyme renin acts on a blood plasma α-globulin, angiotensinogen, to procude angiotensin I, which is then converted by angiotensin converting-enzyme to AII. The latter substance is a powerful vasopressor agent which has been implicated as a causitive agent for producing high blood pressure in various mammalian species, such as the rat, dog, and man. The compounds of this invention inhibit the action of AII at its receptors on target cells and thus prevent the increase in blood pressure produced by this hormone-receptor interaction. By administering a compound of this invention to a species of mammal with hypertension due to AII, the blood pressure is reduced. The compounds of this invention are also useful for the treatment of congestive heart failure.

K. Matsumura, et al., in U.S. Pat. No. 4,207,324 issued June 10, 1980 discloses 1, 2-disubstituted-4-haloimidazole-5-acetic acid derivatives of the formula:

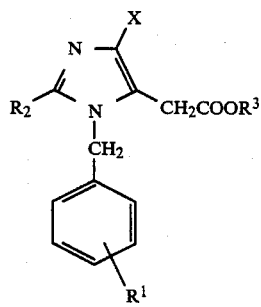

wherein $R^1$ is hydrogen, nitro or amino; $R^2$ is phenyl, furyl or thienyl optionally substituted by halogen, lower alkyl, lower alkoxy or di-lower alkylamino; $R^3$ is hydrogen or lower alkyl and X is halogen; and their physiologiclly acceptable salts. These compounds have diuretic and hypotensive actions.

Furukawa, et al., in U.S. Pat. No. 4,355,040 issued Oct. 19, 1982 discloses hypotensive imidazole-5-acetic acid derivatives having the formula:

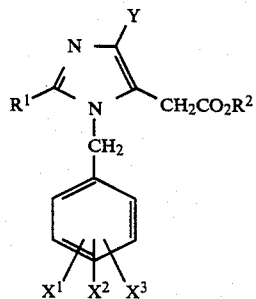

wherein $R^1$ is lower alkyl, cycloalkyl, or phenyl optionally substituted; $X^1$, $X^2$, and $X^3$ are each hydrogen, halogen, nitro, amino, lower alkyl, lower alkoxy, benzyloxy, or hydroxy; Y is halogen and $R^2$ is hydrogen or lower alkyl; and salts thereof.

Furukawa, et al., in U.S. Pat. No. 4,340,598, issued July 20, 1982, discloses hypotensive imidazole derivatives of the formula:

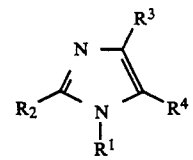

wherein $R^1$ is lower alkyl or, phenyl $C_{1-2}$ alkyl optionally substituted with halogen or nitro; $R^2$ is lower alkyl, cycloalkyl or phenyl optionally substituted; one of $R^3$ and $R^4$ is $-(CH_2)_nCOR^5$ where $R^5$ is amino, lower alkoxyl or hydroxyl and n is 0, 1, 2 and the other of $R^3$ and $R^4$ is hydrogen or halogen; provided that $R^1$ is lower alkyl or phenethyl when $R^3$ is hydrogen, $n=1$ and $R^5$ is lower alkoxyl or hydroxyl; and salts thereof.

Furukawa et al., in European patent application No. 103,647 discloses 4-chloro-2-phenylimidazole-5-acetic acid derivatives useful for treating edema and hypertension of the formula:

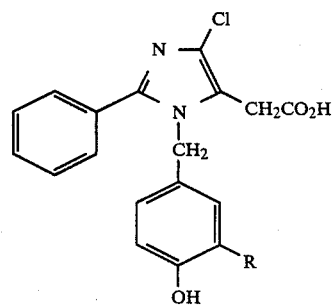

where R represents lower alkyl and salts thereof.

The metabolism and disposition of hypotensive agent 4-chloro-1-(4-methoxy-3-methylbenzyl)-2-phenylimidazole-5-acetic acid is disclosed by H. Torii in Takeda Kenkyushoho, 41, No. 1, 180–191 (1982).

Copending U.S. patent application Ser. No. 884,920 filed July 11, 1986, now abandoned, discloses antihypertensive imidazoles of the formula.

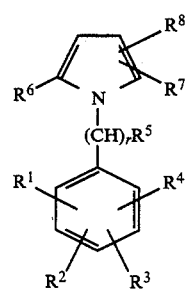

where

-continued $R^1$ is —4-CO$_2$H; —CO$_2$R$^9$; —O—S(=O)(OH)—OH; —SO$_3$H;

—C(CF$_3$)$_2$OH; —C(CF$_3$)$_2$NH$_2$; —O—P(=O)(OH)—OH; —PO$_3$H;

—4-NHSO$_2$R$^{10}$; —CONHOR$^{11}$; —NHCOR$^{12}$; —NHNO$_2$;

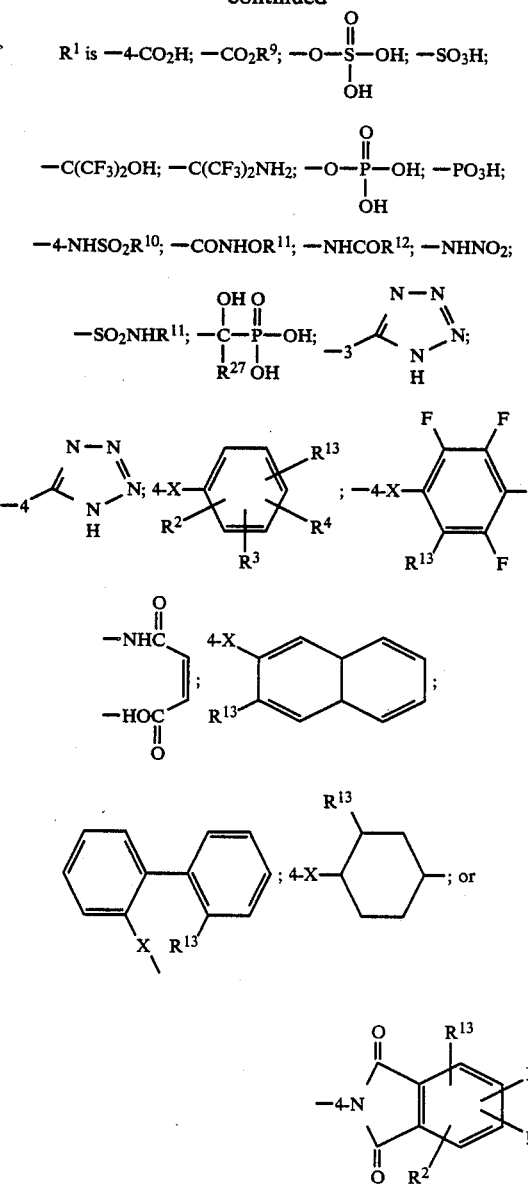

$R^2$, $R^3$ and $R^4$ are each independently H; Cl; Br; I; F; NO$_2$; alkyl of 1 to 4 carbon atoms; alkoxy of 1 to 4 atoms; CO$_2$H; CO$_2$R$^9$; NHSO$_2$R$^{10}$; CONHOR$^{11}$; NHCOR$^{12}$; NHNO$_2$; SO$_2$NHR$^{11}$;

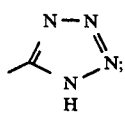

aryl; or furyl;

$R^5$ is H; alkyl of 1 to 6 carbon atoms; allyl benzyl;
$R^6$ is alkyl of 3 to 10 carbon atoms, alkenyl or perfluoroalkyl of 3 to 10 carbon atoms; cycloalkyl of 3 to 8 carbon atoms; cycloalkylalkyl, cycloalkylalkenyl of 4 to 10 carbon atoms; ech of the above groups containing 0 or 1 —O—, —S—, —SO—, —SO$_2$, or —NH— linkage optionally substituted with 0 or 1 groups selected from F, Cl, Br, I, —OR$^{11}$ or —CO$_2$R$^{14}$; phenyl or benzyl optionally substituted with 0 to 2 halogens, alkoxy of 1 to 4 carbon atoms, alkyl of 1 to 4 carbon atoms or nitro; perfluorophenyl;

$R^7$ is H, F, Cl, Br, I, NO$_2$, CF$_3$ or CN;
$R^8$ is alkyl of 1 to 10 carbon atoms, containing 0 or 1 —O—, —S—, —SO, —SO$_2$, or NH; phenyl-alkenyl wherein the aliphatic portion is 2 to 6 carbon atoms, alkenyl of 3 to 10 carbon atoms,

CONR$^{18}$R$^{19}$, —(CH$_2$)$_m$-imidazol-1-yl, —(CH$_2$)$_m$-1,2,3-triazoyl optionally substituted with one or two groups selected from CO$_2$R$^{14}$ or alkyl of 1 to 4 carbon atoms, —(CH$_2$)$_m$-tetra-zolyl,

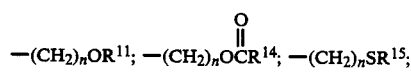

—(CH$_2$)$_n$OR$^{11}$; —(CH$_2$)$_n$OCR$^{14}$(=O); —(CH$_2$)$_n$SR$^{15}$;

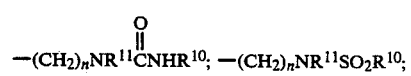

—(CH$_2$)$_n$CR$^{16}$(=O); —(CH$_2$)$_n$OCNHR$^{10}$(=Y); —(CH$_2$)$_n$NR$^{11}$COR$^{10}$;

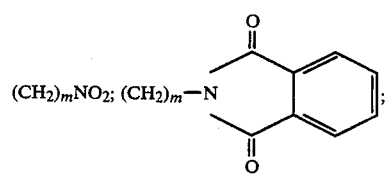

—(CH$_2$)$_n$NR$^{11}$CNHR$^{10}$(=O); —(CH$_2$)$_n$NR$^{11}$SO$_2$R$^{10}$;

—(CH$_2$)$_n$NR$^{11}$CR$^{10}$(=O); —(CH$_2$)$_m$F; (CH$_2$)$_m$ONO$_2$;

(CH$_2$)$_m$NO$_2$; (CH$_2$)$_m$—N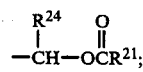;

$R^9$ is

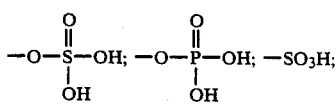

$R^{10}$ is alkyl of 1 to 6 carbon atoms or perfluoroalkyl of 1 to 6 carbon atoms, or (CH$_2$)$_p$C$_6$H$_5$;
$R^{11}$ is H, alkyl of 1 to 6 carbon atoms, cycloalkyl of 3 to 6 carbon atoms, phenyl or benzyl;
$R^{12}$ is perhaloalkyl of 1 to 6 carbon atoms;
$R^{13}$ is —CO$_2$H; —CO$_2$R$^9$;

—O—S(=O)(OH)—OH; —O—P(=O)(OH)—OH; —SO$_3$H;

—PO$_3$H; —C(CF$_3$)$_2$OH; —C(CF$_3$)$_2$NH$_2$; —NHSO$_2$R$^{10}$; —CONHOR$^{11}$; —NHCOR$^{12}$; NHNO$_2$; —SO$_2$NHR$^{11}$;

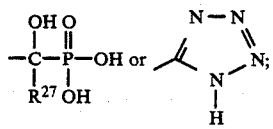 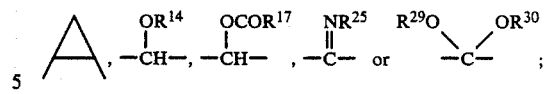

$R^{14}$ is H, alkyl or perfluoroalkyl of 1 to 8 carbon atoms, cycloalkyl of 3 to 6 carbon atoms, phenyl or benzyl;

$R^{15}$ is H, alkyl of 1 to 6 carbon atoms, cycloalkyl of 3 to 6 carbon atoms, phenyl, benzyl, acyl of 1 to 4 carbon atoms, phenacyl;

$R^{16}$ is H, alkyl of 1 to 5 carbon atoms, cycloalkyl of 3 to 6 carbon atoms, $(CH_2)_pC_6H_5$, $OR^{17}$, or $NR^{18}R^{19}$;

$R^{17}$ is H, alkyl of 1 to 5 carbon atoms, cycloalkyl of 3 to 6 carbon atoms, or phenyl;

$R^{18}$ and $R^{19}$ independently are H, alkyl of 1 to 4 carbon atoms, pheny;, benzyl or taken together form a ring of the formula

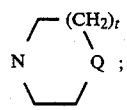

Q is $NR^{20}$, O or $CH_2$;

$R^{20}$ is H, alkyl of 1–4 carbon atoms, or phenyl;

$R^{21}$ is alkyl of 1 to 6 carbon atoms, $-NR^{22}R^{23}$, or

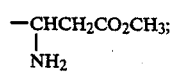

$R^{22}$ and $R^{23}$ independently are H, alkyl of 1 to 6 carbon atoms, benzyl, or are taken together as $(CH_2)_u$ where u is 3–6;

$R^{24}$ is H, $CH_3$ or $-C_6H_5$;

$R^{25}$ is $NR^{27}R^{28}$, $OR^{28}$, $NHCONH_2$, $NHCSNH_2$,

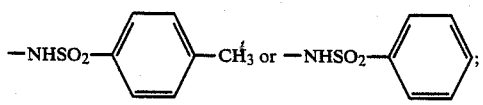

$R^{26}$ is hydrogen, alkyl with from 1 to 6 carbonatoms, benzyl, or allyl;

$R^{27}$ and $R^{28}$ are independently hydrogen, alkyl with from 1 to 5 carbon atoms, or phenyl;

$R^{29}$ and $R^{30}$ are independently alkyl of 1–4 carbon atoms or taken together are $-(CH_2)_q-$;

X is a carbon-carbon single bond, $-CO-$, $-O-$, $-S-$,

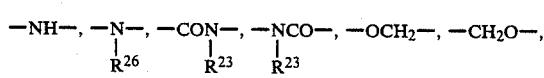

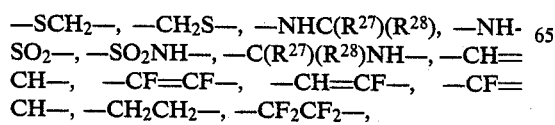

Y is O or S;
m is 1 to 5;
n is 1 to 10;
p is 0 to 3;
q is 1 to 3;
r is 0 to 2;
s is 0 to 5;
t is 0 or 1;

and pharmaceutically acceptable salts of these compounds;

provided that:
(1) the $R^1$ group is not in the ortho position and when $R^1$ is $CO_2H$, then it is also not in the meta position;
(2) when $R^1$ is

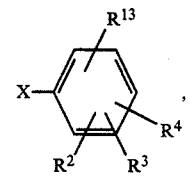

X is a single bond, and $R^{13}$ is $CO_2H$,

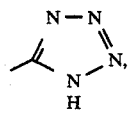

then $r^{13}$ must be in the ortho or meta position; or when $R^1$ and X are as above and $R^{13}$ is $NHSO_2R^{10}$, $R^{13}$ must be ortho;

(3) when $R^1$ is

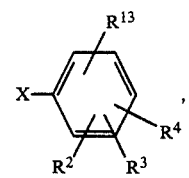

and X is other than a single bond, then $R^{13}$ must be ortho except when X $=NR^{17}CO$ and $R^{13}$ is $NHSO_2R^{10}$, then $R^{13}$ must be ortho or meta;

(4) when $R^1$ is 4-$CO_2H$ or a salt thereof, $R^6$ cannot be S-alkyl;

(5) when $R^1$ is 4-$CO_2H$ or a salt thereof, the substituent on the 4-position of the imidazole cannot be $CH_2OH$, $CH_2OCOCH_3$, or $CH_2CO_2H$;

(6) when $R^1$ is

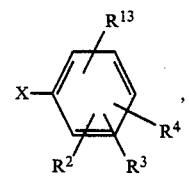

X is —NR[17]CO, and R[13] is 2-CO$_2$H, then R[6] cannot be C$_6$H$_5$(CH$_2$)$_3$;

(7) when R[1] is

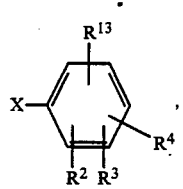

X is —CH$_2$O—, and R[13] is 2-CO$_2$H, then R[6] is not C$_2$H$_5$S or (C$_6$H$_5$)$_2$CH(CH$_2$)$_2$S.

Copending U.S. patent application Ser. No. 050,341 filed May 22, 1987 as a continuation-in-part of U.S. Ser. No. 884,920, and U.S. patent application Ser. No. 07/142,580, filed simultaneously herewith, as a continuation-in-part of U.S. Ser. No. 050,341, also disclose antihypertensive imidazoles. U.S. application Ser. No. 07/141,669 filed simultaneously herewith, discloses antihypertensive, pyrroles, pyrazoles and triazoles.

Pals et al., *Circulation Research*, 29, 673 (1971) describe that the introduction of a sarcosine residue in position 1 and alanine in position 8 of the endogenous vasoconstrictor hormone AII to yield an (octa)peptide that blocks the effects of AII on the blood pressure of pithed rats. This analog, [Sar[1], Ala[8]] AII, initially called "P-113" and subsequently "Saralasin", was found to be one of the most potent competitive antagonists of the actions of AII, although, like most of the so-called peptide-AII-antagonists, it also possessed agonistic actions of its own. Saralasin has been demonstrated to lower arterial pressure in mammals and man when the (elevated) pressure is dependent on circulating AII (Pals et al., *Circulation Research*, 29, 673 (1971); Streeten and Anderson, Handbook of Hypertension, Vol. 5, Clinical Pharmacology of Antihypertensive Drugs, A. E. Doyle (Editor), Elsevier Science Publishers B.V., p. 246 (1984). However, due to its agonistic character, saralasin generally elicits pressor effects when the pressure is not sustained by AII. Being a peptide, the pharmacological effects to saralasin are relatively short-lasting and are only manifest after parenteral administration, oral doses being ineffective. Although the therapeutic uses of peptide AII-blockers, like saralasin, are severely limited due to their oral ineffectiveness and short duration of action, their major utility is as a pharmaceutical standard.

To date there are no known non-peptide antagonists of AII which are useful orally or which bind in vitro in the IC$_{50}$ ranges we observe, other than the compounds disclosed in U.S. Ser. Nos. 884,920 and 050,341, and in the two applications filed simultaneously herewith which are mentioned above.

SUMMARY OF THE INVENTION

According to the present invention there are provided novel compounds of formula (1) which have angiotensin II-antagonizing properties and are useful as antihypertensives.

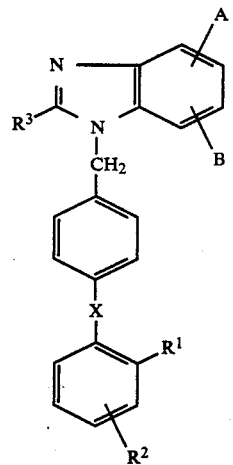

where
R[1] is —CO$_2$H, —NHSO$_2$CF$_3$, or

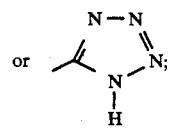

R[2] is H, halogen, NO$_2$, methoxy, or alkyl of 1 to 4 carbon atoms;

R[3] is alkyl of 1 to 6 carbon atoms, alkenyl or alkynyl of 3 to 6 carbon atoms both of which may be optionally substituted with a halogen atom, —OR[4] or up to two —CO$_2$R[4]; with the proviso that when R[3] is methyl it must be substituted with —OR[4] or —CO$_2$R[4];

R[4] is H, or alkyl of 1-4 carbon atoms;

R[5] is H, alkyl of 1 to 5 carbon atoms, cycloalkyl of 3 to 6 carbon atoms, (CH$_2$)$_m$C$_6$H$_5$, OR[6], or NR[7]R[8];

R[6] is H, alkyl of 1 to 5 carbon atoms, cycloalkyl of 3 to 6 carbon atoms or phenyl;

R[7] and R[8] independently are H, alkyl of 1 to 4 carbon atoms, phenyl, benzyl or taken together with nitrogen form a ring of the formula

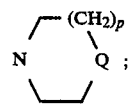

Q is NR[9], O, or CH$_2$;
R[9] is H, alkyl of 1 to 4 carbon atoms, or phenyl;
R[10] is alkyl of 1 to 6 carbon atoms;
A is H, alkyl of 1 to 10 carbon atoms, C$_r$F$_{2r+1}$ where r=1-6, C$_6$F$_5$, halogen, alkoxy of 1 to 6 carbon atoms;

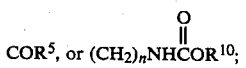

B is H, alkyl of 1 to 10 carbon atoms, $C_rF_{2r+1}$ where $r=1-6$, $C_6F_5$, halogen or alkoxy of 1 to 6 carbon atoms;

X is a carbon-carbon single bond, —CO—, —O—, —NHCO—, or —OCH$_2$—;

n is 1 to 6;

m is 0 to 3;

p is 0 to 1;

and pharmaceutically acceptable salts of these compounds;

provided that:

(1) when $R^3$ is methyl it must be substituted with —OR$^4$ or —CO$_2$R$^4$;

(2) when $R^3$ is —CH=CH—CO$_2$Et, then X is not —NHCO.

(3) when $R^3$ is CH$_2$OH, CH=CHCO$_2$H or CH$_2$CH$_2$CO$_2$H and A and B arae hydrogen, then X cannot be a carbon-carbon single bond.

(4) when $R^1$ is —CO$_2$H, $R^3$ is butyl, and X is a carbon-carbon single bond, then A is not 5-Cl.

(5) when $R^1$ is —CO$_2$H, $R^3$ is CH$_2$OCH$_3$ and X is a carbon-carbon single bond, then A is not 5-CH$_2$OH.

Preferred for their antihypertensive activity are benzimidazoles of Formula (1) and pharmaceutically acceptable salts of these compounds. where:

$R^1$ is —CO$_2$H, —NHSO$_2$CF$_3$;

or 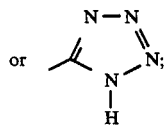

$R^2$ is hydrogen;

$R^3$ is alkyl of 3 to 6 carbon atoms, alkenyl or alkynyl of 3 to 6 carbon atoms each of which may be optionally substituted with —OR$^4$ or CO$_2$R$^4$;

$R^5$ is H, alkyl of 1 to 5 carbon atoms, OR$^6$ or NR$^7$R$^8$;

$R^6$ is H, alkyl of 1 to 5 carbon atoms;

A is halogen, alkoxy of 1 to 6 carbon atoms;

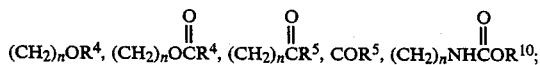

B is H; and pharmaceutically acceptable salts thereof.

More preferred are compounds of the preferred scope where:

$R^3$ is alkyl of 3 to 5 carbon atoms, alkenyl or alkynyl of 3 to 5 carbon atoms each of which may be optionally substituted with OH, OCH$_3$, CO$_2$H or CO$_2$CH$_3$;

$$A \text{ is Cl, OCH}_3, (CH_2)_n OH, (CH_2)_n O\overset{O}{\overset{\|}{C}}CH_3, CHO, CO_2H,$$

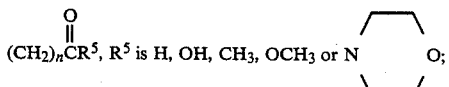

n is 1-2;

X is a carbon-carbon single bond; or —NHCO—; and pharmaceutically acceptable salts thereof.

Specifically preferred compounds because of their antihypertensive activity are:

(a) 2-Butyl-1-[(2'-carboxybiphenyl-4-yl)methyl]-6-hydrozymethylbenzimidazole
(b) 2-Butyl-1-[(2'-carboxybiphenyl-4-yl)methyl]-5-hydroxymethylbenzimidazole
(c) 2-Butyl-1-[(2'-carboxybiphenyl-4-yl)methyl]-6-methoxybenzimidazole
(d) 2-(1-Butenyl)-1-[(2'-carboxybiphenyl-4-yl)methyl]-6-hydroxymethylbenzimidazole;
(e) 2-Butyl-1-[(2'-carboxybiphenyl-4-yl)methyl]-6-chlorobenzimidazole; and pharmaceutically suitable salts thereof.

Pharmaceutically suitable salts include both the metallic (inorganic) salts and organic salts; a list of which is given in *Remington's Pharmaceutical Sciences*, 17th Edition, page 1418 (1985). It is well known to one skilled in the art that an appropriate salt form is chosen based on physical and chemical stability, flowability, hygroscopicity and solubility. Preferred salts of this invention for the reasons cited above include potassium, sodium, calcium and ammonium salts.

Also within the scope of this invention are pharmaceutical compositions comprising a suitable pharmaceutical carrier and a compound of Formula (1), processes for preparing the compounds and methods of using the compounds of Formula (1) to treat hypertension, and congestive heart failure.

Note that throughout the text when an alkyl substituent is mentioned, the normal alkyl structure is meant (i.e., butyl is n-butyl) unless otherwise specified.

It should be noted that, in the foregoing structural formula, when a substituent can be present in more than one position it can be selected independently at each occurrence. For example, if $R^4$ is present as part of both the definition of $R^3$ and A and/or B it need not be defined as the same substituent.

Synthesis

The novel compounds of Formula (1) can be prepared using the reactions and techniques described in this section. The reactions are performed in a solvent appropriate to the reagents and materials employed and suitable for the transformation being effected. It is understood by those skilled in the art of organic synthesis that the functionality present on the benzimidazole and other portions of the molecule must be consistent with the chemical transformations proposed. This will frequently necessitate judgment as to the order of synthetic steps, protecting groups required, and deprotection conditions. Throughout the following section, not all compounds of Formula (1) falling into a given class may necessarily be prepared by all methods described for that class. Substituents on the starting materials may be incompatible with some of the reaction conditions required in some of the methods described. Such restrictions to the substituents which are compatible with the reaction conditions will be readily apparent to one skilled in the art and alternative methods described must then be used.

Generally, the compounds of formula (1) can be prepared by direct alkylation onto benzimidazole (2) with an appropriately protected benzyl halide, tosylate or mesylate (3) in the presence of base as shown in Scheme I. Preferably, the metallic benzimidazolide salt is prepared by reacting benzimidazole (2) with a proton acceptor such as MH where M is lithium, sodium or potassium in a solvent such as dimethylformamide (DMF) or by reacting it with a metal alkoxide of formula MOR where R is methyl, ethyl, t-butyl or the like in an alcohol solvent such as ethanol or t-butanol, or a polar aprotic solvent such as DMF. The benzimidazole salt is dissolved in an inert aprotic solvent such as DMF, and treated with an appropriate alkylating agent (3). Alternatively, benzimidazole (1) can be alkylated with a benzyl halide (3; where Y=Br or Cl) in the presence of a base such as sodium carbonate, potassium carbonate, triethylamine or pyridine. The reaction is run in an inert solvent such as DMF or DMSO at 20° C. to the refluxing temperature of the solvent for 1–10 hours.

When A and B are not equivalent, mixtures of two regioisomer alkylation products are obtained. These isomers possess distinct physical and biological properties and can be separated and isolated by conventional separation techniques such as chromatography and/or crystallization.

An alternative synthesis for benzimidazole compounds of formula (1) is described in Scheme II.

Scheme I:

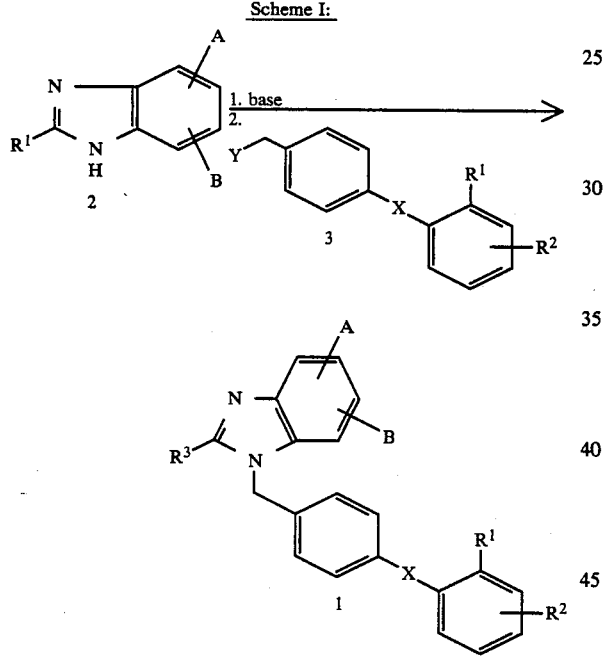

Scheme II:

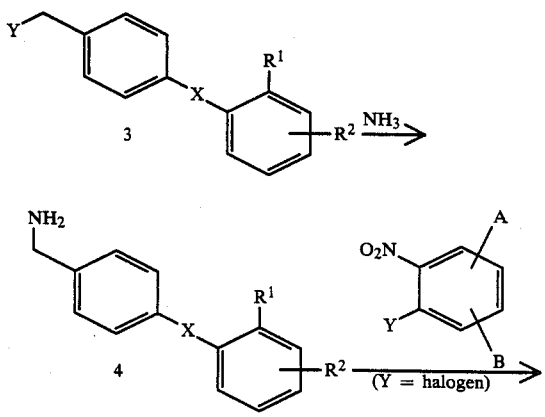

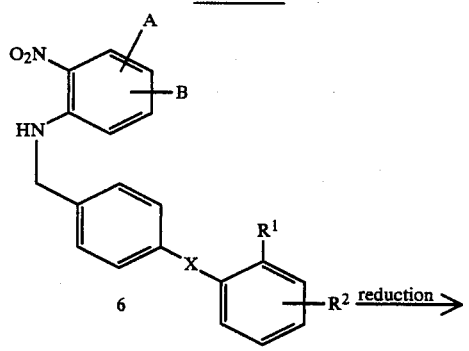

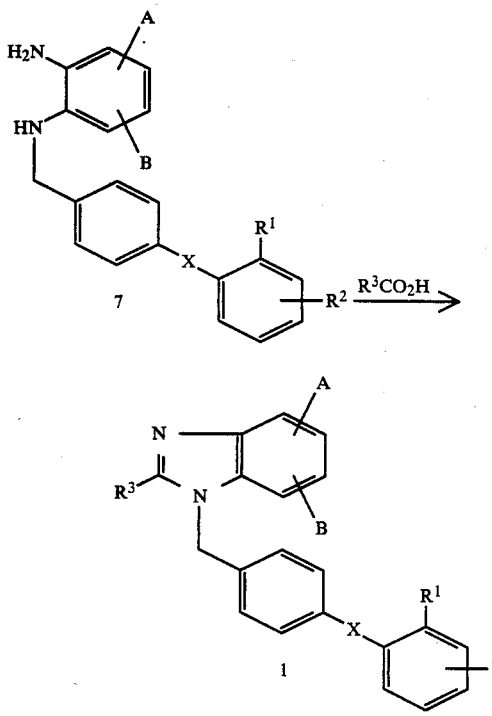

The functionalized benzylamines (4) can be made from the corresponding benzyl halide, tosylate or mesylate (3) via displacement with a nitrogen nucleo-phile, a procedure familiar to one skilled in the art. This displacement may be achieved using azide ion, ammonia, or phthalimide anion, etc., in a neutral solvent such as DMF, DMSO etc., or under phase transfer conditions. The benzyl halide (3) can be made by a variety of benzylic halogenation methods familiar to one skilled in the art, for example benzylic bromination of toluene derivatives with N-bromosuccinimide in an inert solvent such as carbon tetrachloride in the presence of a radical initiator such as benzoyl peroxide at temperatures up to reflux conditions.

Reaction of a benzylamine (4) with an o-halogen substituted nitrobenzene (5) affords the corresponding nitro compound (6).

O-Phenylenediamine intermediates (7) can be obtained from the corresponding nitro compounds (6) by reduction. A variety of reduction procedures may be used such as Fe/acetic acid [D. C. Owsley, J. J. Bloomfield, *Synthesis*, 118 (1977)], stannous chloride [F. D.

Bellamy, *Tetrahedron Lett.*, 839 (1984)] or careful hydrogenation over a metal catalyst such as palladium.

Reaction of (7) with a carboxylic acid under a variety of conditions some of which are described in the disclosure for Scheme III, equation (b) provides the desired compound (1).

The benzimidazole compounds (2) are readily available by any of a number of standard methods. Several of these synthetic routes are illustrated in Scheme III.

As shown in Scheme III, equation (a), a variety of benzimidazoles can be prepared by reduction of acylated o-nitroanilines (8) with various reducing agents such as Sn/HCl [H. Hubner, Ann., 208, 278 (1881)]SnCl$_2$/HCl [L. I. Smith, et al., *J. Am. Chem. Soc.*, 57, 1289 (1935)], and Fe/acetic acid [M. A. Phillips, *J. Chem. Soc.*, 2393 (1928)]. Another method for the conversion of an acylated o-nitroaniline into a 2-substituted benzimidazole (1) involves heating the compound with ferrous oxalate at a temperature in the range of 220°–225° C. [H. C. Waterman, et al., *J. Org. Chem.*, 14, 289 (1949)]. The transformation of an acylated o-nitroaniline into a benzimidazole (2) can also be effected by electrolytic reduction [K. Brand, et al., Ber. 39, 4058 (1906)] or by catalytic hydrogenation [R. Adams, et al., *J. Am. Chem. Soc.*, 70, 2667 (1948)].

Alternatively, benzimidazoles (2) can be synthesized by reacting an o-phenylenediamine and a carboxylic acid [M. A. Phillips, *J. Chem Soc.*, 1409 (1930)], or an acid anhydride as shown in Scheme III, equation (b). One method involves refluxing an equimolar mixture of a substituted o-phenylenediamine and a carboxylic acid or an acid anhydride in dilute hydrochloric acid. Benzimidazole (2) can also be prepared by reaction of an appropriately substituted o-phenylenediamine and an ester. Reaction of an acid amide and an o-phenylenediamine as described in S. Von Niementowski, Ber., 30, 3062 (1897) also results in the formation of benzimidazoles of formula (2).

Alternatively, as shown in Scheme III equation (c), heating the hydrochloride salt of an o-phenylene-diamine with a nitrile at elevated temperatures (~200° C.) results in the formation of a 2-substituted benzimidazole (2) [E. L. Holljes and E. C. Wagner, *J. Org. Chem.*, 9, 31 (1944)].

Benzimidazole (2) can also be prepared by reaction of o-phenylenediamine with an iminoether or an iminothioester as shown in equation (d) [F. E. King et al., *J. Chem. Soc.*, 1396 (1949)].

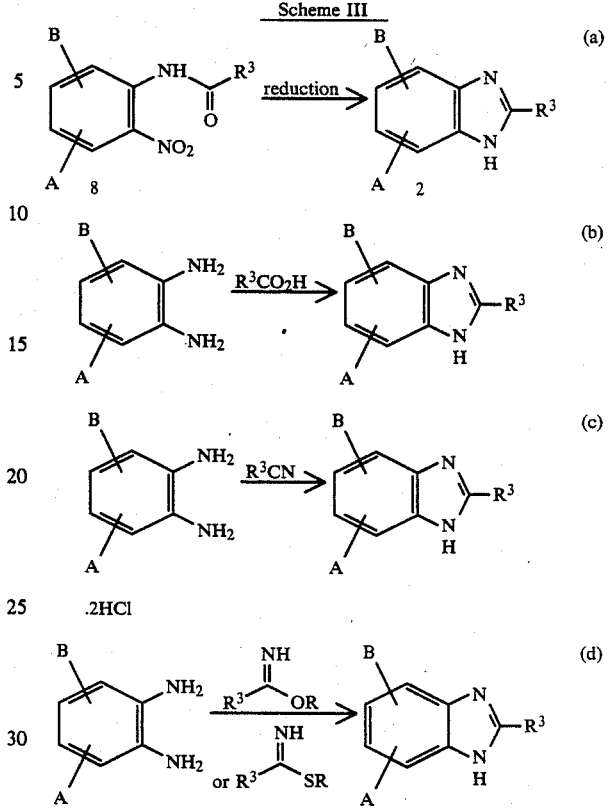

Substituents A and B can be incorporated into the benzene ring at the beginning of the synthesis such that the desired compounds (2) can be obtained via Scheme III, or A and B can be derived from suitable synthetic precursors at a later stage in the synthesis.

As shown in Scheme IV, the hydroxymethyl groups can be easily converted to the corresponding halide, mesylate or tosylate moieties by a variety of methods familiar to one skilled in the art. Preferably, alcohol (9) is converted to the chloride (11) with thionyl chloride in an inert solvent at temperatures of 20° C. to the reflux temperature of the solvent. Alkylation of (9) with alkyl halides in the presence of a base such as sodium hydride in a solvent such as THF or glyme at 0°–80° C. gives (10).

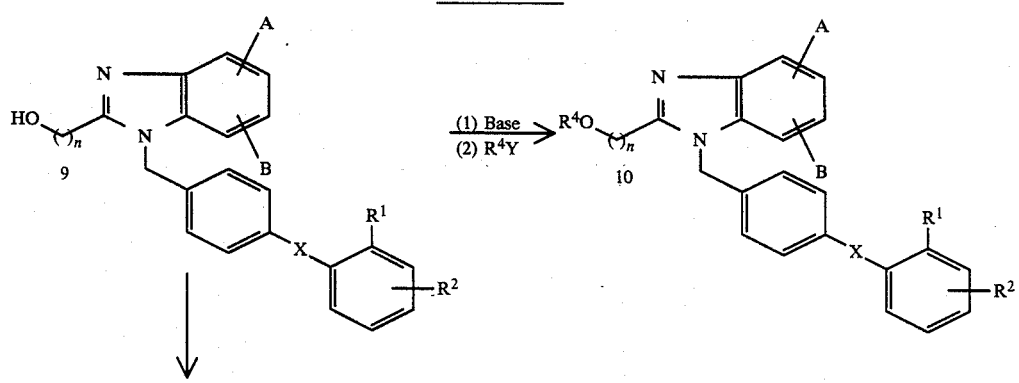

-continued
Scheme IV

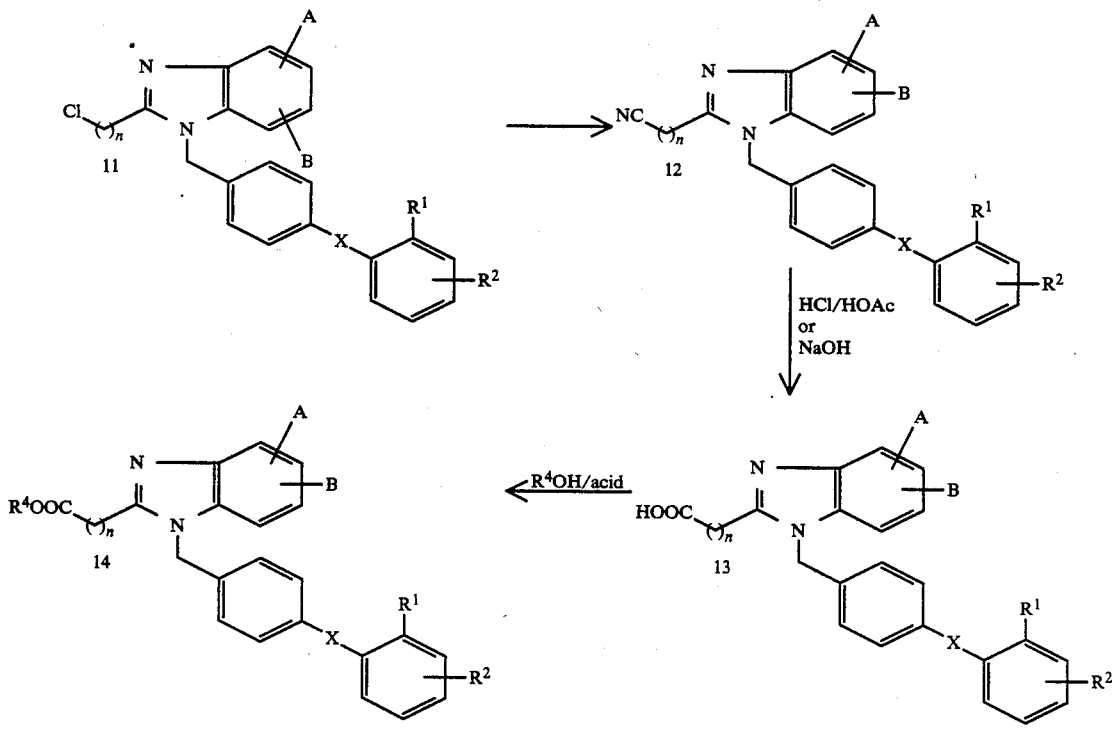

Chloride (11) may be displaced by a variety of nucleophiles by nucleophilic displacement reaction procedures, familiar to one skilled in the art. For example, excess sodium cyanide in DMSO may be used to form cyanomethyl derivatives (12) at temperatures of 20° C. to 100° C.

Nitrile intermediate (12) can be hydrolyzed to carboxylic acid derivative (13) by a variety of methods. Preferably, treatment with a 1:1 (v:v) mixture of concentrated aqueous HCl/glacial acetic acid at reflux temperatures for 2–96 hours or by treatment with 1~6N sodium hydroxide in an alcohol solvent such as ethanol or ethylene glycol for 2–96 hours at temperatures from 20° C. to reflux can be used. The nitrile functionality can also be hydrolyzed in two steps by first stirring in sulfuric acid to form the amide followed by hydrolysis with sodium hydroxide or a mineral acid to give the carboxylic acid (13).

Carboxylic acid (13) can be esterified by a variety of methods without affecting other parts of the molecule. Preferably, (13) is refluxed in a mixture of HCl and an alcohol solution for 2–48 hours to give esters (14).

The hydroxymethyl group on compound (9) can be readily oxidized to an aldehyde group by means of an oxidizing agent such as manganese dioxide as shown in Scheme V. The aldehyde (15) will undergo chain extension reactions such as the Wittig and Wittig-Horner reactions, and enter into typical carbon-carbon bond forming reactions with Grignard and lithium reagents as well as with compounds bearing activated methylene groups, known to one skilled in the art of organic synthesis.

Scheme V

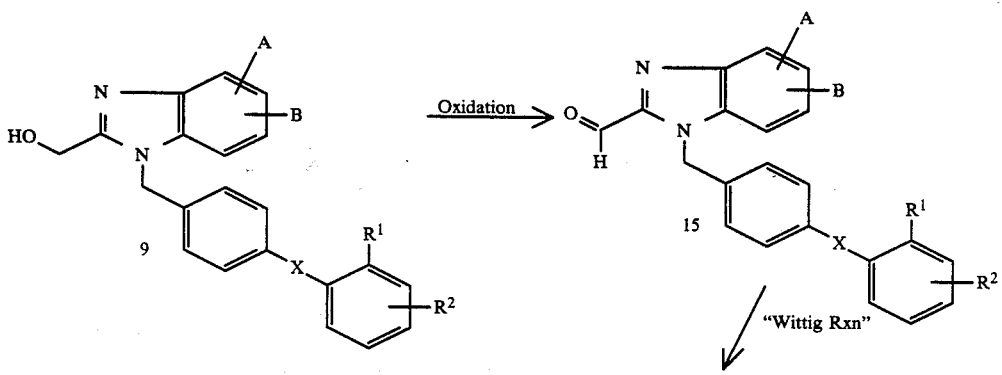

-continued
Scheme V
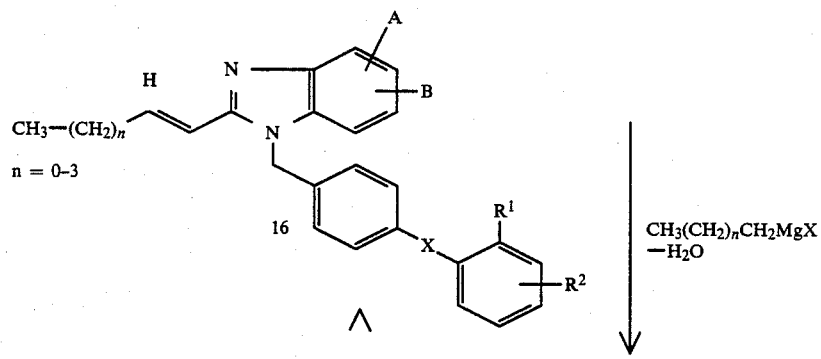
The ether (18) can be prepared from the alcohol (17) as shown in Scheme VI, equation (a) by methods such as treatment of (17) in a solvent such as DMF or DMSO with potassium t-butoxide, sodium hydride, or the like followed by treatment with $R^4Y$ at 25° C. for 1–20 hours, where Y is a halogen, tosylate or mesylate.
Scheme VI
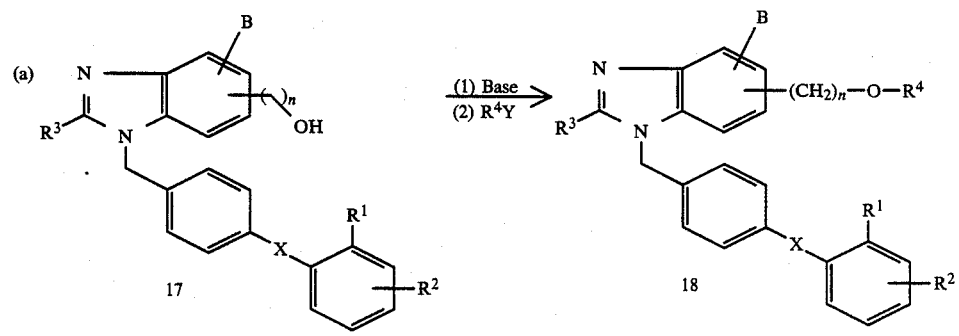
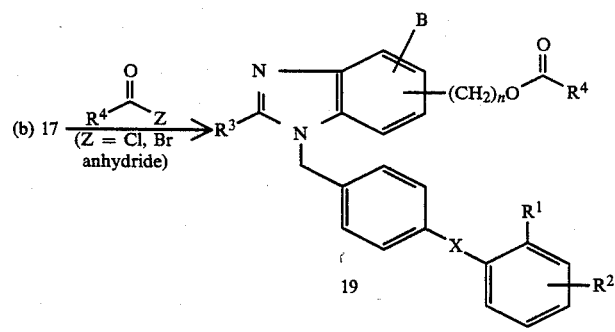
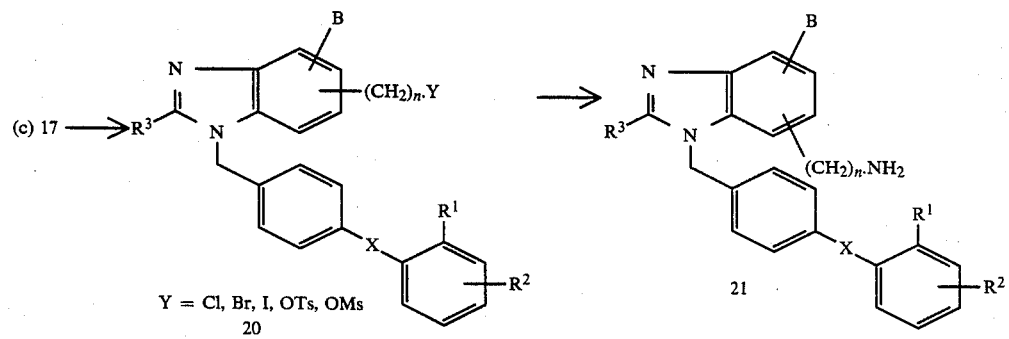

-continued
Scheme VI

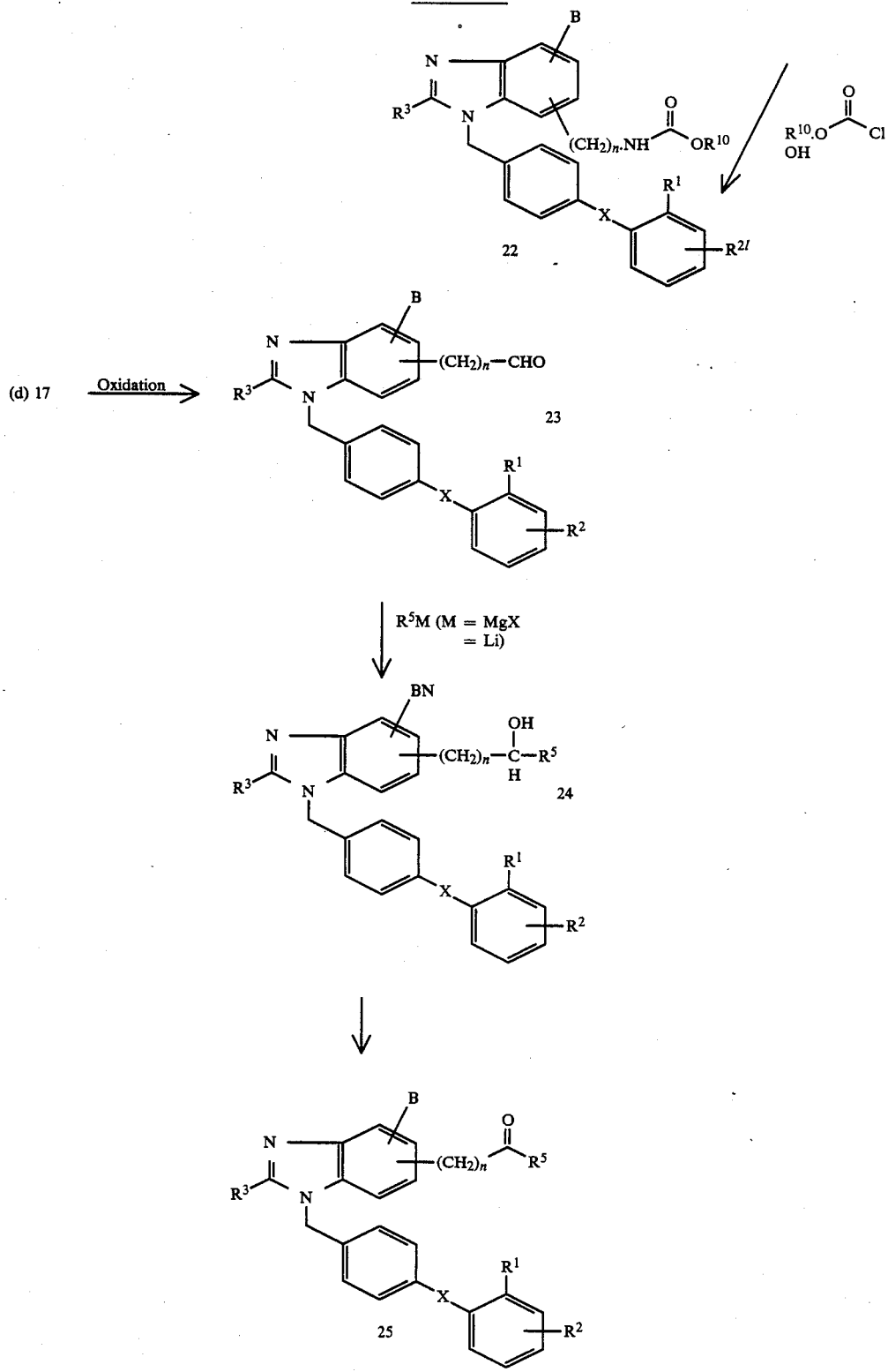

Hydroxymethyl derivative (17) may be acylated to give (19) by a variety of procedures. As shown in Scheme VI, equation (b), acylation can be achieved with 1~3 equivalents of an acyl halide or an anhydride in a solvent such as diethyl ether, tetrahydrofuran, methylene chloride or the like in the presence of a base such as pyridine or triethylamine. Alternatively, (17) may be acylated by reaction with a carboxylic acid and dicyclohexylcarbodiimide (DCC) in the presence of a catalytic amount of 4-(N,N-dimethylamino)pyridine (DMAP) via the procedure described by A. Hassner, *Tetrahedron Lett.*, 4475 (1978). Treatment of (17) with a solution of carboxylic acid anhydride in pyridine optionally with a catalytic amount of DMAP at temperatures of 20°–100° C. for 2–48 hours is the preferred method.

The hydroxymethyl group in compound (17) can be activated for displacement by reacting it with thionyl chloride; $PCl_5$ or with carbon tetrachloride/triphenylphosphine to form the corresponding chloro-derivative. By a similar reaction, bromo and iodo derivatives can be obtained. The hydroxymethyl group can also be activated by forming the corresponding p-toluenesulfonate, methanesulfonate and trifluoromethane sulfonate derivatives as illustrated in Scheme VI, equation (c).

The amino derivative (21) can be obtained by treating compound (20) with ammonia. Alternatively, the chloro group can be displaced by sodium azide to give an azide intermediate which affords the amine (21) upon reduction with hydrogen ($H_2$) over a noble metal catadard procedures familiar to one skilled in the art as illustrated by equation (c).

The hydroxymethyl compound (17) can be oxidized to aldehyde (23) by treatment with an oxidizing agent such as manganese dioxide. Reaction of aldehyde (23) with an appropriate Grignard reagent affords alcohol (24) which can be oxidized to ketone derivative (25) by standard oxidizing procedures familiar to one skilled in the art.

The halomethylbiphenyl ether (29) is prepared as shown in Scheme VII. An Ullman ether condensation of the phenol (26) and a halobenzoic acid as described in *Russian Chemical Reviews,* 43, 679 (1974) provides the intermediate carboxylic acid (27). The conversion of (27) into (28) is accomplished by diazomethane or by a Fischer esterification method.

Halogenation to give halomethyldiphenylether (29) can be accomplished by refluxing (28) in an inert solvent such as carbon tetrachloride in the presence of a N-halosuccinimide and an initiator such as azobisisobutyronitrile.

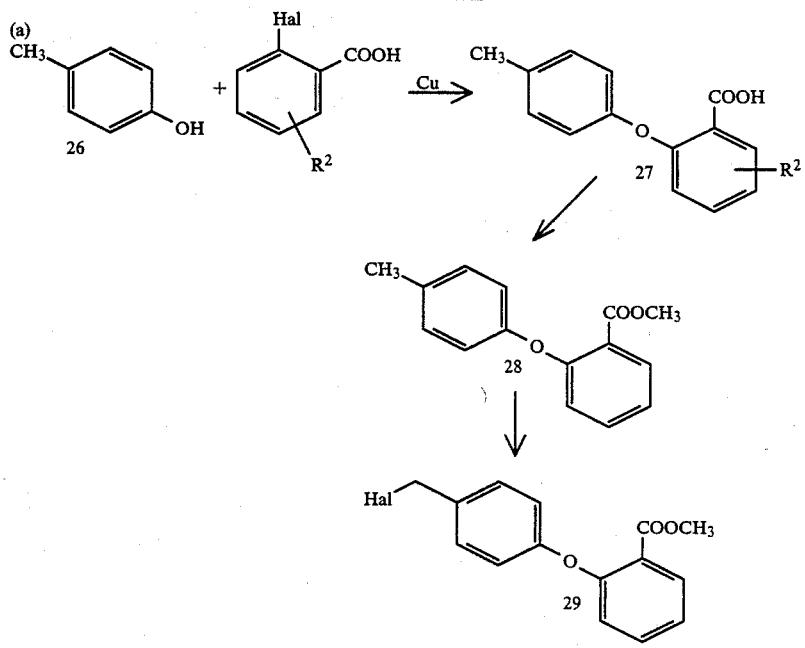

Scheme VII lyst or with a reducing agent such as chromous chloride [W. K. Warburton, *J. Chem. Soc.,* 2651 (1961)]. The amine (21) can be converted to carbamate (22) by stan- Compounds (1) where the X linkage is a carbon-carbon bond are prepared by alkylation of benzimidazole (2) with suitable halomethyl biphenyl intermediates (30), as shown in Scheme VIII.

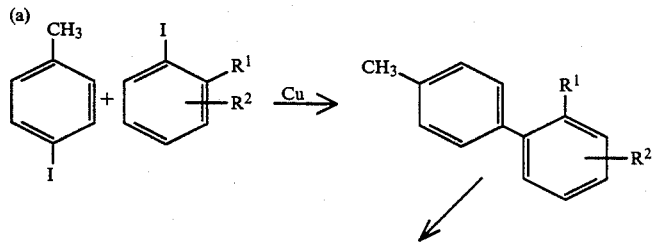

Scheme VIII

Scheme VIII -continued

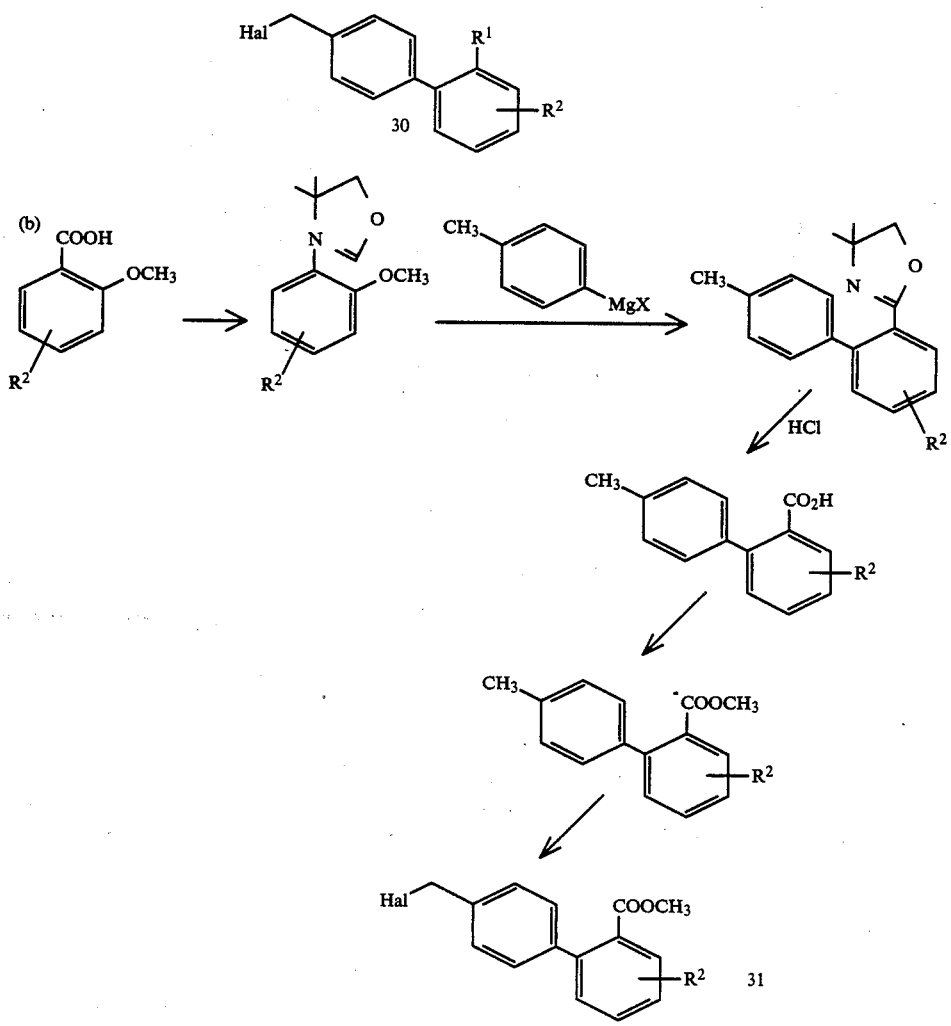

The halomethylbiphenyl intermediates (30) are prepared by Ullman coupling of two iodobenzene derivatives as described in "Organic Reactions", 2, 6 (1944) to provide intermediates which are in turn halogenated to provide (30).

Alternatively, the substituted biphenylprecursors (31), where $R^1$=o—$CO_2CH_3$ can be prepared as illustrated in Scheme VIII, path (b), which involves oxazoline compounds as key intermediates [A. I. Meyers and E. D. Michelich, J. Am. Chem. Soc., 97, 7383 (1975)].

As shown in Scheme IX, compounds where X is —CO— can be prepared by alkylation of imidazoles (2) with the requisite benzoylbenzyl halides. Carboalkoxybenzoylbenzyl halides (32) are prepared by benzylic halogenation of the corresponding toluoylbenzene precursors (33) by a variety of methods known to one skilled in the art. For example, methyl-2-(4-methylbenzoyl) benzoate can be refluxed for 2–48 hours with N-bromosuccinimide, benzoylperoxide and carbon tetrachloride to effect benzylic bromination. After alkylation of the imidazole with the benzoylbenzyl halide of compound (34), the ester group can be hydrolyzed to the corresponding carboxylic acid (35) with a base such as sodium hydroxide or potassium hydroxide in an alcoholic aqueous solvent such as methanol/$H_2O$.

Scheme IX

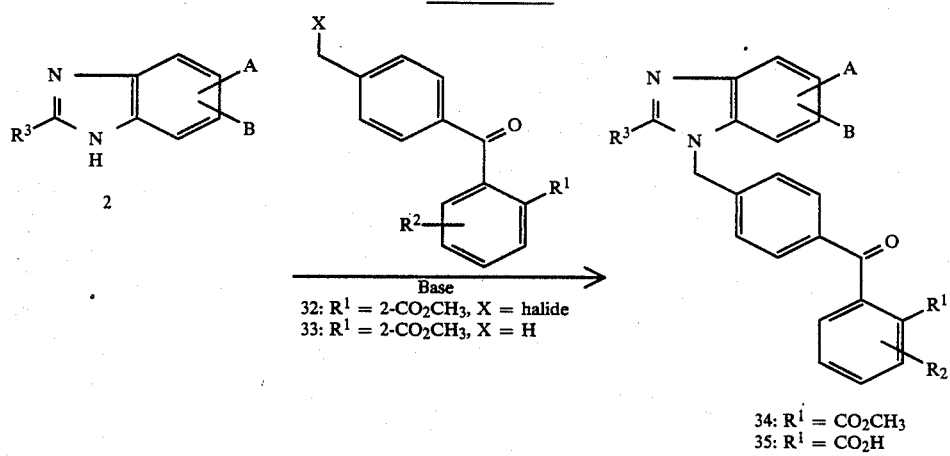

34: R¹ = CO₂CH₃
35: R¹ = CO₂H

As shown in Scheme X, compound (38) in which R¹=CO₂H can be easily prepared, for example, by reacting aniline precursor (37) with a phthalic anhydride derivative in an appropriate solvent such as benzene, chloroform, ethyl acetate, etc. [M. L. Sherrill, F. L. Schaeffer, E. P. Shoyer, *J. Am. Chem. Soc.*, 50, 474 (1928)].

The 4-nitrobenzylintermediate (36) can be obtained by direct alkylation onto benzimidazole with a 4-nitrobenzyl halide, tosylate or mesylate in the presence of a base such as sodium hydride.

When R¹ is NHSO₂CF₃ or tetrazolyl, compound (38) can be obtained by reacting aniline (37) with the requisite acid chloride by either a Schotten-Baumann procedure, or simply stirring in a solvent such as methylene chloride in the presence of a base such as sodium bicarbonate, pyridine, or triethylamine.

Likewise, aniline (37) can be coupled with an appropriate carboxylic acid via a variety of amide or peptide bond forming reaction such as DCC coupling, azide coupling, mixed anhydride synthesis, or any other coupling procedure familiar to one skilled in the art.

-continued
Scheme X

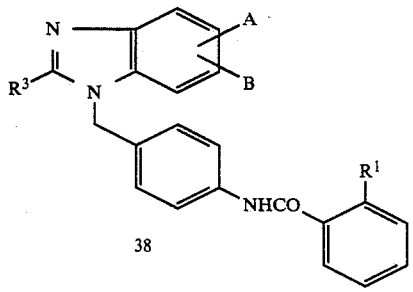

Compounds of formula (1) where X is —OCH₂ are prepared as shown in Scheme XI.

Scheme X

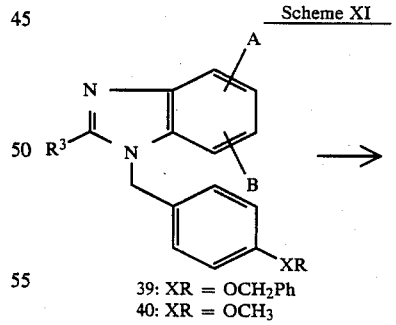

Scheme XI

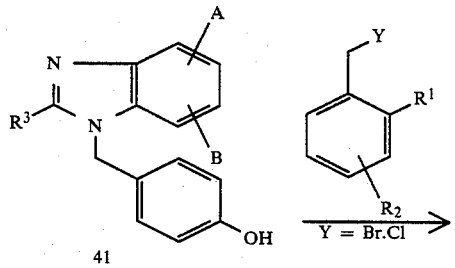

39: XR = OCH₂Ph
40: XR = OCH₃

-continued
Scheme XI

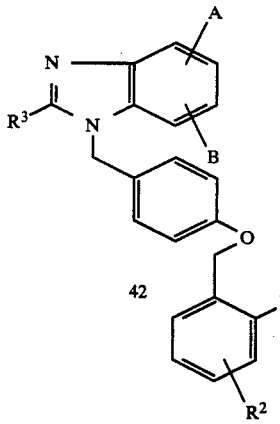

As illustrated in Scheme XI, hydrolysis of benzylether (39) or methyl ether (40) affords hydroxy compound (41) which can be alkylated with the appropriate benzyl halide to give (42). In the case of the methyl ethers (40), the hydrolysis step can be effected by heating the ether at temperatures of 50°–150° C. for 1–10 hours in 20–60% hydrobromic acid, or heating at 50°–90° C. in acetonitrile with 1–5 equivalents of trimethylsilyl iodide for 10–50 hours followed by treatment with water. Hydrolysis can also be carried out by treatment with 1–2 equivalents of boron tribromide in methylene chloride at 10°–30° C. for 1–10 hours followed by treatment with water, or by treatment with an acid such as aluminum chloride and 3–30 equivalents of sulfur-containing compound such as thiophenol, ethanedithiol, or dimethyl disulfide in methylene chloride at 0°–30° C. for 1–20 hours followed by treatment with water. For compound (39), hydrolysis can be accomplished by refluxing in trifluoroacetic acid for 0.2–1 hours or by catalytic hydrogenolysis in the presence of a suitable catalyst such as 10% palladium on carbon. Deprotonation of (41) with a base, such as sodium methoxide, sodium hydride or the like in a solvent such as dimethylformamide or dimethylsulfoxide at room temperature followed by alkylation with an appropriated benzyl halide at 25° C. followed by stirring for 2–20 hours affords ethers of formula (42).

The compounds of this invention and their preparation can be understood further by the following examples, but should not constitute a limitation thereof. In these examples, unless otherwise indicated, all temperatures are in degrees centigrade.

Example 1

Preparation of
3-[1-(4-(2-Carboxybenzamido)benzyl)benzimidazol-2-yl]-2-(carboethoxy)propanoic acid, ethyl ester Part A: Preparation of
1-(4-Nitrobenzyl)-2-hydroxymethylbenzimidazole To a solution of 3 g of 2-hydroxymethylbenzimidazole in 20 mL of dried DMF at 0° was added portionwise 1 g of NaH (50% oil dispersion). After stirring at room temperature for 15 minutes, 4.3 g of p-nitrobenzyl bromide was added. The reaction mixture was stirred for 16 hours and then diluted with ethyl acetate and washed with water. The organic layers were dried and evaporated. Recrystallization from acetonitrile afforded 3.5 g of a brownish solid; m.p. 162.5–165°.

Part B: Preparation of
1-(4-Nitrobenzyl)-2-chloromethylbenzimidazole

To a solution of 2.2 g 1-(4-nitrobenzyl)-2-hydroxymethylbenzimidazole in 30 mL of chloroform was added 3.3 mL of thionyl chloride. The reaction mixture was stirred at room temperature for 18 hours and then concentrated in vacuo. The residue was taken up in water, neutralized with K$_2$CO$_3$ to a pH of 10 and extracted into methylene chloride. The organic layer was dried over Na$_2$SO$_4$ and concentrated to give 2 g of 1-(4-nitrobenzyl)-2-chloromethylbenzimidazole as a yellowish solid.

Part C: Preparation of
3-[1-(4-Nitrobenzyl)benzimidazol-2-yl]-2-(carboethoxy)propanoic acid, ethyl ester The sodium salt of diethylmalonate was generated from 0.35 g of NaH (50% oil dispersion) and 1.1 mL of diethyl malonate in 15 mL of dried DMF with ice cooling. To the above mixture was added 2 g of 1-(4-nitrobenzyl)-2-chloromethylbenzimidazole and the mixture was stirred at room temperature for 18 hours. The reaction mixture was diluted with ethyl acetate, washed with water, dried and concentrated in vacuo. The crude produce was purified by flash column chromatography (hexane/ethyl acetate, 1:1) to give a yellowish thick oil which was crystallized from absolute ethanol to give a white solid; m.p. 135°.

Part D:
3-[1-(4-Aminobenzyl)benzimidazol-2-yl]-2-(carboethoxy)propanoic acid, ethyl ester A mixture of 0.28 g of the compound of Part C, 0.20 g or iron, 0.4 g of glacial acetic acid, and 3 mL of ethanol was refluxed for 4 hours. The reaction mixture was diluted with water and extracted with ethyl acetate. The organic layers were dried and concentrated. The residue was flash chromatographed (ethyl acetate) to afford the amine as a slightly brownish liquid.

Part E

A mixture of 40 mg of the amine from Part D in 2 mL of chloroform was treated with 15 mg of phthalic anhydride. The reaction mixture was stirred at room temperature for 16 hours and then concentrated to dryness. The residue was purified by flash column chromatography (5% methanol/methylene chloride) to afford the title compound as a waxy solid.
$^1$H NMR(CDCl$_3$)δ: 7.67 (m, 2H), 7.50 (d, 4H), 7.22 (d, 4H), 6.93 (d, 2H), 5.37 (s, 2H), 4.33 (t, 1H), 3.37 (d, 2H), 1.13 (t, 6H).

EXAMPLE 2

Preparation of
3-[1-(4-(2-Carboxybenzamido)benzyl)benzimidazole-2-yl]-2-propanoic acid, ethyl ester Part A: Preparation of 3-[1-(4-Nitrobenzyl)benzimidazol-2-yl]-2-prpanoic acid A mixture of 0.425 g of the malonate derivative obtained from Part C of Example 1; 1 mL of aqueous 4N sodium hydroxide and 20 mL of methanol ws stirred at room temperature for 16 hours. The reaction mixture was concentrated and the residue dissolved in 30 mL of water. The aqueous layer was acidified with hydrochloric acid to a pH of 4. The resulting solids were collected, washed with water and air dried to afford 0.3 g of the product; m.p. 123°–125° (dec; loss of $CO_2$). The solids (0.3 g) were heated to 135° at which temperature the reaction mixture bubbled and $CO_2$ gas was given off. The thick gummy residue was used in the next reaction without purification.

Part B: Preparation of 3-[1-(4-Nitrobenzyl)benzimidazol-2-yl]-2-propanoic acid, ethyl ester The propanoic acid derivative (0.25 g) was dissolved in 20 mL of 3% hydrochloric acid in ethanol and the reaction mixture was refluxed for 16 hours. The reaction mixture was concentrated and the residue was dissolved in 50 mL of water which was taken to a pH of 10 with $Na_2CO_3$. The aqueous mixture was extracted with ethyl acetate and then washed with water and dried. Concentration of the ethyl acetate layer gave the crude methyl ester as a thick oil. Purification by flash column chromatography (hexane/ethyl acetate/methylene chloride, 1:3:1) afforded 0.2 g of product as a brownish solid.

Part C

The nitro compound of Part B (0.18 g) was reduced to the corresponding aniline derivative by the procedure described in Example 1, Part D. To the aniline compound (65 mg) in 3 mL of chloroform was added 30 mg of phthalic anhydride and the reaction mixture was stirred at room temperature for 16 hours. The reaction mixture was concentrated and triturated with ether. The resulting solids were collected and dried to afford 0.08 g of the title compound; m.p. 95°–97° (dec.)

EXAMPLE 3

Preparation of 1-[4-(2-Carboxybenzamido)benzyl]-2-(1-pentenyl)benzimidazole Part A: Preparation of 1-(4-Nitrobenzyl)benzimidazole-2-carboxaldehyde A mixture of 0.71 g of 1-(4-nitrobenzyl)-2-hydroxymethylbenzimidazole and 0.2 g of activated $MnO_2$ in 20 mL of chloroform was stirred at room temperature for 6 hours. The reaction mixture was then filtered through celite and the filtrate was concentrated. Purification by flash column chromatography on silica get (ethyl acetate) afforded the desired aldehyde as a yellowish solid; m.p. 141°–141.5°.

Part B: Preparation of 1-(4-Nitrobenzyl-2-(1-pentenyl)benzimidazole

A mixture of 0.4 g of n-butyltriphenylphosphonium bromide in 20 mL of anhydrous tetrahydrofuran was cooled to −50°. To this was added 0.6 mL of 1.6M n-butyllithium (in hexane) dropwise. After stirring at−50° for 10 minutes, 0.25 g of the aldehyde from Part A was added and the reaction mixture was allowed to warm up to room temperature and stirred for 2 hours. The reaction mixture was quenched with 2 mL of saturated $NH_4Cl$ solution and diluted with ethyl acetate. The ethyl acetate solution was washed with water, brine, dried and concentrated to dryness. Purification by flash column chromatography (silica gel, hexane/ethyl acetate, 1:1) afforded the desired compound.

Part C: Preparation of 1-(4-Aminobenzyl)-2-(1-pentenyl)-benzimidazole

The nitro compound (30 mg) obtained from Part B was reduced to the corresponding aniline derivative via the procedure described in Part D of Example 1. Purification by flash column chromatography on silica gel afforded 15 mg of the amine.

Part D

The title phthalamic acid derivative was obtained by treatment of the aniline derivative of Part C with phthalic anhydride by the method described in Part E of Example 1; m.p. 153°–154.5°.

EXAMPLE 4

Preparation of 3-[1-(4-(2-Carboxybenzamido)benzyl)benzimidazol-2-yl]propenoic acid, ethyl ester Part A: Preparation of 3-[1-(4-Nitrobenzyl)benzimidazol-2-yl]propenoic acid, ethyl ester A mixture of 0.21 g of the aldehyde of Example 3, Part A and 0.26 g of (carbethoxymethylene)triphenylphosphorane in 5 mL of benzene was stirred at room temperature for 30 minutes. The reaction mixture was concentrated and the residue was purified by flash column chromatography on silica gel (hexane/ethyl acetate, 1.5:1) to afford 0.22 g of the desired compound.

Part B: Preparation of 3-[1-(4-Aminobenzyl)benzimidazol-2-yl]propenoic acid, ethyl ester A mixture of 0.5 g of the compound of Part A, 0.125 g or iron, 0.25 mL glacial acetic acid in 20 mL of absolute ethanol was refluxed for 30 minutes. The reaction mixture was concentrated to dryness and the residue was diluted with 5 mL of water and the solution was made basic by adding $K_2CO_3$. The mixture was extracted with ethyl acetate. The organic layer was concentrated to give 35 mg of a crude product which was used in the next step without purification.

Part C

The title phthalamic acid derivative was obtained via the treatment of the aniline derivative of Part B (32 mg) with phthalic anhydride (15 mg) by the method described in Part E of Example 1; m.p. 196–197 (dec).

EXAMPLE 5

Preparation of 3-[1-(4-(N-trifluoromethanesulfonyl)anthranilamido)-benzyl)benzimidazol-2-yl]propenoic acid, ethyl ester A mixture of 0.22 g of the aniline compound of Example 4, Part B, and 0.3 mL of triethylamine and a catalytic amount of dimethylaminopyridine in 10 mL of methylene chloride was cooled with an ice bath. To the reaction mixture was added 0.25 g of o-(trifluoromethanesulfonamido)benzoyl chloride dropwise followed by stirring at room temperature for 16 hours. The reaction mixture was concentrated and the residue was taken up in ethyl acetate. The ethyl acetate solution was washed with water, brine, dried and concentrated to give a crude product which was purified by flash silica gel column chromatography (ethyl acetate/acetonitrile, 5:1) to give the title compund as a thick oil. $^1H$ NMR $(CDCl_3)\delta:8.10–7.00$ (many peaks, 14H), 5.48 (s, 2H), 4.30 (q, 2H), 1.33 (t, 3H).

EXAMPLE 6

Preparation of
3-[1-(4-((N-Trifluoromethanesulfonyl)anthranilamido)-
benzyl)benzimidazol-4-yl]propranoic acid, ethyl ester A mixture of 0.350 g of the compound of Example 5, 0.10 g of 10% palladium/carbon and 30 mL of absolute ethanol was stirred for 4 hours at room temperature under 1 atm of $H_2$ gas. The reaction mixture was filtered through celite, and the filtrate was concentrated in vacuo. The thick product was purified by flash column chromatography on silica gel (5% acetonitrile/ethyl acetate) to give the title compound as a thick colorless oil.

Examples 1–26 in Table 1 were prepared or can be prepared by the procedures described in Examples 1–6 and by the methods described hereinabove from the appropriate benzimidazole starting materials.

TABLE 1

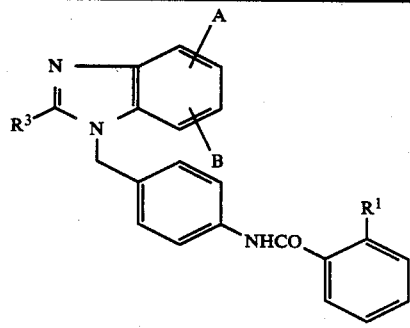

| Ex. No. | $R^1$ | $R^3$ | A | B | m.p. (°C.) |
|---|---|---|---|---|---|
| 1 | —CO₂H | —CH₂CH(CO₂Et)₂ | H | H | * |
| 2 | —CO₂H | —CH₂CH₂CO₂Et | H | H | 95–97 (dec) |
| 3 | —CO₂H | (pentenyl) | H | H | 153–154.5 |
| 4 | —CO₂H | (=CH-CO₂Et alkenyl) | H | H | 196–197 (dec) |
| 5 | NHSO₂CF₃ | (=CH-CO₂Et alkenyl) | H | H | * |
| 6 | NHSO₂CF₃ | —(CH₂)₂CO₂Et | H | H | |
| 7 | —CO₂H | n-butyl | H | H | |
| 8 | —CO₂H | n-propyl | H | H | |
| 9 | —CO₂H | n-butyl | 5-OCH₃ | H | |
| 10 | —CO₂H | n-butyl | 6-OCH₃ | H | |
| 11 | —CO₂H | n-butyl | 5-OCH₃ | 6-OCH₃ | |
| 12 | —CO₂H | n-butyl | 5-Cl | H | |
| 13 | —CO₂H | n-propyl | 6-Cl | H | |
| 14 | —CO₂H | n-butyl | 5-CH₃ | H | |
| 15 | —CO₂H | n-butyl | 5-CF₃ | H | |
| 16 | —CO₂H | n-butyl | 5-CHO | H | |
| 17 | —CO₂H | n-butyl | 5-CH₂OH | 6-CH₃ | |
| 18 | —CO₂H | n-propyl | 6-CH₂OH | H | |
| 19 | —CO₂H | n-butyl | 6-C₂H₅ | H | |
| 20 | —CO₂H | n-butyl | 5-CH₂NHCOCH₃ | H | |
| 21 | (tetrazolyl) | n-butyl | H | H | |
| 22 | (tetrazolyl) | n-butyl | 6-OCH₃ | H | |
| 23 | (tetrazolyl) | n-propyl | 5-Cl | 6-Cl | |
| 24 | (tetrazolyl) | n-pentyl | 6-CH₂OH | H | |

TABLE 1-continued

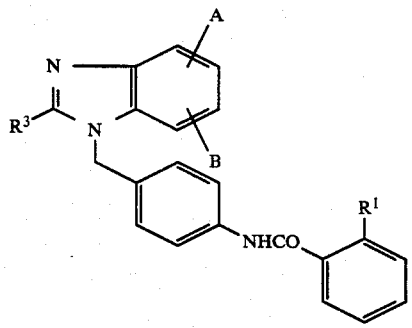

| Ex. No. | R¹ | R³ | A | B | m.p. (°C.) |
|---|---|---|---|---|---|
| 25 | NHSO₂CF₃ | n-butyl | 6-OCH₃ | H | |
| 26 | NHSO₂CF₃ | n-propyl | 6-CH₂OH | H | |

*NMR data given in experimental procedure for Examples 1 and 5.

EXAMPLE 27

2-Butyl-1-[(2'-Carboxybiphenyl-4-yl)methyl]-6-hydroxymethylbenzimidazole

Part A: Preparation of 3-methyl p-valeroylamidobenzoate

A mixture of 6 g of methyl 4-aminobenzoate, 7 mL of dried pyridine (stored under KOH pellets) and a catalytic amount of p-dimethylaminopyridine in 100 mL of methylene chloride (CH$_2$Cl$_2$) was cooled with ice. To the above solution was added dropwise 5.5 mL of valeryl chloride. After all of the acid chloride was added, the reaction mixture was warmed to room termperature and stirred for an additional 2 hours. The reaction mixture was evaporated to dryness and the residue was taken up in 250 mL of ethyl acetate (EtOAc). The EtOAc layer was washed with water (100 mL), 5% copper sulfate (CuSO$_4$) solution (3×100 mL), water (100 mL) and finally with brine solution. The EtOAc layer was dried over sodium sulfate (Na$_2$SO$_4$) and concentrated to give 8.2 g of a crude product as an amorphous solid. $^1$H NMR (CDCl$_3$) δ: 7.61 & 8.0 (dd, J=8.5 Hz, 2H each); 7.52 (broad s, 1H); 3.9 (s, 3H); 2.39 (t, J=7.5 Hz, 2H); 1.7 (m, 2H); 1.4 (sex, J=7.3 Hz, 2H); 0.94 (t, J=7.3 Hz, 3H).

Part B: Preparation of methyl 3-nitro-4-valeroylamidobenzoate

Methyl p-valeroylamidobenzoate (8 g) was dissolved in 11 mL of concentrated sulfuric acid (H$_2$SO$_4$) and the solution was maintained in an ice bath. To the above solution was added a mixture of nitric acid (HNO$_3$; 3.5 mL, 70%) and concentrated sulfuric acid (H$_2$SO$_4$; 3.5 mL) at such a rate to keep the reaction temperature below 15°. The reaction mixture was then allowed to stir at room temperature for 2 hours. The reaction mixture was carefully poured onto approximately 40 g of ice. The resulting solid was collected by filtration and was washed with water until the filtrate was neutral. The solids were then air-dried and then dried under vacuum to give 7.8 g of tan solids; m.p. 94°–96°. $^1$H NMR (CDCl$_3$) δ: 11.07 (s, 1H); 8.23–9.0 (m, 3H); 2.53 (t, J=7 Hz, 2H); 1.77 (m, 2H); 1.45 (m, 2H); 0.97 (t, J=7.3 Hz, 3H).

Part C: 2-Butyl-6-carbomethoxybenzimidazole

A mixture of 5 g methyl 3-nitro-4-valeroylamido-benzoate, 5 g or iron powder and 10 mL of glacial acetic acid in 40 mL of absolute ethanol was refluxed for 2 hours. The reaction mixture was concentrated and the residue was dissolved in 50 mL of water. The aqueous solution was then neutralized to pH 8 by careful addition of sodium bicarbonate (NaHCO$_3$) powder. The mixture was then extracted into 300 mL of EtOAc. The EtOAc layer was then washed with H$_2$O (2×100 mL) and brine (100 mL). Concentration of the EtOAc layer gave a crude product which was purified by flash silica gel column chromatography (Hexane: EtOAc, 1:1) to afford 2.8 g of the desired product; m.p. 108°–109.5°. $^1$H NMR (CDCl$_3$) δ: 8.29 (broad s); 7.95 (dd, J=8.8 Hz & 1.4 Hz, 1H); 7.55 (broad d, J=7.8 Hz, 1H); 3.93 (s, 3H); 2.98 (t, J=7.5 Hz, 2H); 1.86 (m, 2H); 1.35 (m, 2H); 0.875 (t, J=7.3 Hz, 3H).

Part D: Preparation of 2-Butyl-6-hydroxymethylbenzimidazole

A solution of 2.1 g of 2-butyl-6-carbomethoxybenzimidazole in 50 mL of tetrahydrofuran was cooled with ice. To this solution was added dropwise 18 mL of 25% diisobutylaluminum hydride (DiBAl-H) in toluene. After the addition, the reacted mixture was stirred for 30 minutes with ice cooling and then for an additional 1 hour at room temperature. The reaction mixture was cooled back down to 0° and the reaction quenched by adding 15 mL of saturated ammonium chloride (NH$_4$Cl) solution. The mixture was then filtered through celite and the filtrate was concentrated. The crude product was purified by silica gel column chromatography (100% EtOAc elution) to give 1.23 g of the desired product as a thick colorless oil.

Part E: Prepartion of 2-Butyl-1-[(2'-carbomethoxybiphenyl-4-yl)methyl]-5(6)-hydroxymethylbenzimidazole A solution of 1.23 g of 2-butyl-6-hydroxymethyl-benzimidazole in 10 mL of dried DMF was cooled to 0°. To this was added 250 mg of 60% NaH portionwise and the mixture was stirred for an additional 15 minutes. To the mixture was added 2.3 g of 4-(2'-carbomethoxyphenyl)-benzylbromide followed by stirring at room temperature for 18 hours. The reaction mixture was concentrated to remove the solvent and the residue was taken into 200 mL of EtOAc. The EtOAc layer was washed with H$_2$O (2×100 mL) and brine (100 mL). Concentration of the EtOAc extracts gave a crude product which was purified by flash column chromatography (silica gel, EtOAc elution). The fast moving isomer was collected and concentrated to give 1.0 g of a colorless solid. $^1$H NMR (CDCl$_3$) δ: 7.0–7.84 (many peaks, 1H); 5.33 (s, 2H); 4.75 (s, 2H); 3.62 (s, 3H); 2.84 (t, J=8.2 Hz, 2H); 1.81 (m, 2H); 1.40 (m, 2H); 0.91 (t, J=7.2 Hz, 3H). The slower moving isomer was collected and concentrated to give 1.0 g of a thick colorless oil which solidified upon standing. The faster moving isomer proved to be significantly less soluble in methanol than the other isomer.

Part F

A mixture of 1 g of the faster moving isomer isolated in Part E, and 1 mL of 50% NaOH (aqueous solution) in 15 mL of methanol was refluxed for 4 hours. The reaction mixture was cooled to room temperature and concentrated to remove the methanol. The residue was dissolved in approximately 20 mL of H$_2$O and the aqueous solution was acidified to pH 5 by adding 1N HCl. The resulting solids were collected, washed with H$_2$O and dried to give 0.8 g of the title compound as a colorless solid; m.p. 124°–126°.

EXAMPLE 28

2-Butyl-1-[(2'-carboxybiphenyl-4-yl)methyl]-5-hydroxymethylbenzimidazole

A mixture of 1.0 g of the slower moving product from Example 27, Part E, and 1 mL of 50% NaOH (aqueous solution) in 15 mL of methanol was refluxed for 4 hours. The reaction mixture was cooled to room temperature and concentrated to remove methanol. The residue was dissolved in approximately 20 mL of H$_2$O and the aqueous solution was acidified to pH 5 by adding 1N HCl. The resulting solids were collected, washed with H$_2$O and dried to give 0.8 g of 2-butyl-1-[(2'-carboxybiphenyl-4-yl)methyl]-5-hydroxymethyl-benzimidazole as a colorless solid; m.p. 130°–143°.

EXAMPLE 29

Preparation of 1-[(2'-Carboxybiphenyl-4-yl)methyl]-2-butyl-6-methoxybenzimidazole Part A: Preparation of 2-Butyl-6-methoxybenzimidazole A mixture of 1.75 g of 4-methoxy-o-phenylenediamine, 2 mL of triethylamine and a catalytic amount of p-dimethylaminopyridine in 20 mL of methylene chrloride was cooled with ice. To the above solution was added 1.3 mL of valeryl chloride dropwise. The reaction mixture was stirred at room temperature for 2 hours and diluted with 100 mL of ethyl acetate, then washed with water and concentrated to give a crude product which was dissolved in 30 mL of absolute ethanol. After 2 mL of glacial acetic acid and a catalytic amount of p-toluenesulfonic acid were added to the above, the solution was refluxed for 18 hours. The reaction mixture was concentrated and the residue was purified by flash column chromatography on silica gel (100% EtOAc elution) to give 0.46 g of the desired product as a thick colorless oil.

Part B: Preparation of 1-[(2'-Carbomethoxybiphenyl-4-yl)methyl]-2-butyl-5(6)-methoxybenzimidazole the methoxybenzimidazole (0.46 g ) from Part A was alkylated with 0.60 g of 4-(2'-carbomethoxyphenyl)benzyl-bromide using the same procedure described in Example 27, Part E. The resulting mixture of isomers was also separated by the same procedure described in Example 27, Part E, to afford 0.26 g of each isomer as a thick oil.

Part C

The faster moving isomer from Part B which was identified by NMR to be 1-[(2'-Carbomethoxybiphenyl-4-yl)methyl]-2-butyl-6-methoxyimidazole was treated with 1.5 mL of 50% NaOH (aqueous solution) in 10 mL of methanol at the reflux temperature for six hours. The reaction mixture was cooled to room temperature and concentrated to dryness. The residue was dissolved in approximately 20 mL of H$_2$O and the aqueous solution was acidified with 1 N HCl to pH 5. The resulting solids were collected, washed with water and dried to give 0.23 g of 1-[(2'-carboxybiphenyl-4-yl)methyl-2-butyl-6-methoxybenzimidazole; m.p. 221°–222.5°.

EXAMPLE 30

2-Butyl-1-](2'-Carboxybiphenyl-4-yl)methyl]-5-methoxybenzimidazole

The title compound (0.23 g) was prepared from the slower moving isomer in Example 29, Part B, by the procedure described in Example 27, Part F; m.p. 194°–195.5°.

EXAMPLE 31

Preparation of 2-Butyl-1-[2'-carboxybiphenyl-4-yl)methyl]benzimidazole-6-carboxaldehyde Part A: Preparation of 2-Butyl-1-[(2'-carbomethoxybiphenyl-4-yl)methyl]benzimidazole-6-carboxaldehyde A mixture of 1.9 g of 2-butyl-1-[(2'-carbomethoxybiphenyl-4-yl)methyl]-6-hydroxymethyl]benzimidazole (prepared as described in Example 27, Part E) and 2.5 g of activated MnO$_2$ in 30 mL of methylene chloride was stirred at room temperature for 4 hours. The reaction mixture was passed through celite and the filtrate was concentrated. The residue was purified via column chromatography (hexane/ethyl acetate, 1:3) to give 1.4 g of the desired compound as thick oil.

Part B

A mixture of 0.2 g of the compound obtained in Part A, 1 mL of 1N NaOH solution, and 4 mL of methanol was refluxed for 4 hours. The reaction mixture was concentrated to dryness, and the residue was diluted with 30 mL of H$_2$O and the pH of the aqueous solution was adjusted to 5–6 with 1N HCl. The resulting solids were collected, washed with H$_2$O and dried to give 0.15 g of the title compound as a pale yellow solid, m.p. 216°–218°.

EXAMPLE 32

Preparation of
2-(1-Butenyl)-6-hydroxymethyl-1-[(2'-carboxybiphenyl-4-yl)methyl]benzimidazole

Part A Preparation of 2-(1-Bromobutyl)-1-[(2'-carboxymethylbiphenyl-4-yl)methyl]benzimidazole-6-carboxaldehyde To a mixture 0.55 g of 2-butyl-1-[(2'-carboxymethylbiphenyl-4-yl)methyl]benzimidazole-6-carboxaldehyde in 30 mL of carbon tetrachloride was added 0.23 g of N-bromosuccinimide and a catalytic amount of azobisisobutyronitrile. The reaction was stirred at room temperature until the reaction went to completion and then concentrated to dryness. The residue was partitioned between ethyl acetate and water. The organic phase was washed with water, dried and concentrated. Flash column chromatography (silica gel; 1:1 hexane/ethyl acetate to 1:3 hexane/ethyl acetate) afforded 0.45 g of the product as a thick clear oil.

Part B: Preparation of 2-(1-Bromobutyl)-1-[(2'-carboxy-methylbiphenyl-4-yl)methyl]-6-hydroxymethylbenz-imidazole A solution of 1.06 g of the compound prepared in Part A in 30 mL of methanol was cooled to 4° and 0.35 g of sodium borohydride (NaBH₄) was added portionwise. After all the NaBH₄ was added, the reaction mixture was stirred for 10 minutes. To the reaction mixture was added saturated NH₄Cl and the mixture was extracted with ethyl acetate, washed with water and then concentrated to dryness. The residue was purified by flash column chromatography (elution:ethyl acetate) to give 0.5 g of a thick clear oil.

Part C: Preparation of 2-(1-Butenyl)-6-hydroxymethyl-1[(2'-carboxymethyl-biphenyl-4-yl)methyl]benzimi-dazole To a stirred solution of 0.25 g of the compound obtained from Part B in 5 mL of methylene chloride was added 0.2 mL of 1,8-diazabicyclo[5.4.0]undec-7-ene (DBU) and the reaction mixture was heated to reflux for 5 hours. The residue was purified by flash column chromatography on silica gel (elution:ethyl acetate) to afford 0.14 g of a thick clear oil.

Part D

A mixture of 75 mg of the compound obtained in Part C, 0.5 mL of 1N NaOH solution, and 5 mL of methanol was refluxed for 4 hours. The reaction mixture was concentrated to dryness, and the residue was diluted with 5 mL of H₂O and the reaction mixture was acidified to a pH of 5–6. The resulting solids were collected, washed with water and dried to give 70 mg of the title compound, m.p. 139°–141°.

Examples 33–68 in Table 2 were prepared or can be prepared by the procedures described in Examples 27–32 and the methods described hereinabove from the appropriately substituted benzimidazole starting materials.

TABLE 2

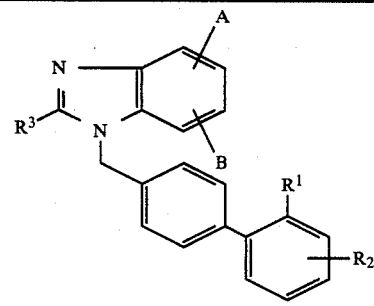

| Ex. No. | R¹ | R² | R³ | A | B | m.p. (°C.) |
|---|---|---|---|---|---|---|
| 27 | —CO₂H | H | n-butyl | 6-CH₂OH | H | 124–126 |
| 28 | —CO₂H | H | n-butyl | 5-CH₂OH | H | 130–132 |
| 29 | —CO₂H | H | n-butyl | 6-OCH₃ | H | 221–222.5 |
| 30 | —CO₂H | H | n-butyl | 5-OCH₃ | H | 194–195.5 |
| 31 | —CO₂H | H | n-butyl | 6-CHO | H | 216–218 |
| 32 | —CO₂H | H | 1-butenyl | 6-CH₂OH | H | 139–141 |
| 33 | —CO₂H | H | n-butyl | 6-Cl | H | 198–200 |
| 34 | —CO₂H | H | —CH₂OCH₃ | 6-CH₂OH | H | 203–204.5 |
| 35 | —CO₂H | H | —CH₂OCH₃ | 5-CH₂OH | H | 96–98 |
| 36 | —CO₂H | H | n-butyl | 5-CO₂H | H | 248–250 |
| 37 | —CO₂H | H | n-butyl | 6-CO₂H | H | 294–296 |
| 38 | —CO₂H | H | n-butyl | 5-Cl | H | 202–204 |
| 39 | —CO₂H | H | n-butyl | 6-CH₂NHCOCH₂CH₂CH₃ | H | |
| 40 | —CO₂H | H | n-propyl | 5-CHO | H | |
| 41 | —CO₂H | H | n-butyl | CH₂COCH₃ | H | |
| 42 | —CO₂H | H | —CH₂COCH₃ | 6-CF₃ | H | |

TABLE 2-continued

| Ex. No. | R¹ | R² | R³ | A | B | m.p. (°C.) |
|---|---|---|---|---|---|---|
| 43 | —CO₂H | H | n-butyl | 5-OCH₃ | 6-OCH₃ | |
| 44 | —CO₂H | H | —≡—CH₂CH₃ | 6-CH₂OH | H | |
| 45 | —CO₂H | H | n-butyl | 6-OCH₂CH₃ | H | |
| 46 | —CO₂H | 3-OCH₃ | n-propyl | 6-CH₂OH | H | |
| 47 | —CO₂H | 3-CH₃ | n-pentyl | 6-CH₂OH | H | |
| 48 | —CO₂H | H | n-butyl | 6-CH₂CH₂C(=O)—N(morpholino) | H | |
| 49 | —CO₂H | H | n-butyl | 6-CH₂CONHC₆H₅ | H | |
| 50 | —CO₂H | H | n-butyl | 6-CH₂CH₂CO₂H | H | |
| 51 | —CO₂H | H | —CH₂CH₂CH₂Cl | 6-CH₃ | H | |
| 52 | —CO₂H | H | n-butyl | 6-CH₂C(=O)—N(morpholino) | H | |
| 53 | —CO₂H | 4-NO₂ | n-butyl | 6-OCH₃ | H | |
| 54 | —CO₂H | 3-Cl | n-butyl | 6-CH₂OH | H | |
| 55 | tetrazol-5-yl | H | n-butyl | 5-CH₂OH | H | |
| 56 | tetrazol-5-yl | H | n-butyl | 6-OCH₃ | H | |
| 57 | tetrazol-5-yl | H | —CH₂CH=CHCH₃ (2-butenyl) | 6-CH₂OH | H | |
| 58 | tetrazol-5-yl | H | n-butyl | 6-CH₂OH | H | |
| 59 | tetrazol-5-yl | H | n-propyl | 5-OCH₃ | 6-OCH₃ | |
| 60 | tetrazol-5-yl | H | n-propyl | CH₂NHCOCH₂CH(CH₃)₂ | H | |

TABLE 2-continued

[Structure: benzimidazole with R³ at 2-position, A and B substituents on benzo ring, N-CH₂-biphenyl with R¹ and R₂ substituents]

| Ex. No. | R¹ | R² | R³ | A | B | m.p. (°C.) |
|---|---|---|---|---|---|---|
| 61 | tetrazol-5-yl (NH) | H | n-propyl | 6-CHO | H | |
| 62 | tetrazol-5-yl (NH) | H | $CH_2COCH_2CH_3$ | 6-OCH₃ | H | |
| 63 | tetrazol-5-yl (NH) | H | n-butyl | 6-COCH₂C₆H₅ | H | |
| 64 | tetrazol-5-yl (NH) | H | n-butyl | 6-CH₂CO₂CH₃ | H | |
| 65 | NHSO₂CF₃ | H | n-butyl | 6-OCH₃ | H | |
| 66 | NHSO₂CF₃ | H | CH₂CH=CHCH₃ | 6-CH₂CH₂OCH₃ | H | |
| 67 | NHSO₂CF₃ | H | n-butyl | 6-CH₂OH | H | |
| 68 | NHSO₂CF₃ | H | n-propyl | 5-CH₂OH | H | |
| 69 | CO₂H | H | CH₂OH | 6-butyl | H | |
| 70 | CO₂H | H | CH₂OH | 6-propyl | H | |
| 71 | tetrazol-5-yl (NH) | H | CH₂OH | 6-propyl | H | |
| 72 | tetrazol-5-yl (NH) | H | CH₂CO₂H | 6-butyl | H | |

Examples such as 73–76 in Table 3 can be prepared by methods described in the schemes of the synthesis disclosure.

TABLE 3

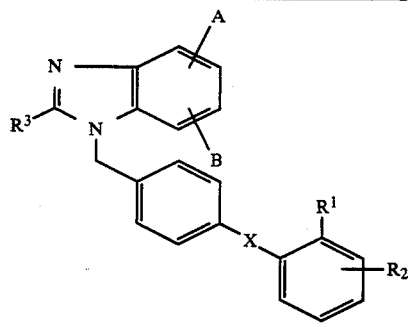

| Ex. No. | R¹ | R² | R³ | X | A | B | m.p. (°C.) |
|---|---|---|---|---|---|---|---|
| 73 | —CO$_2$H | H | n-butyl | CO | 6-CH$_2$OH | H | |
| 74 | —CO$_2$H | H | (CH$_2$CH=CHCH$_2$) | O | 5-CH$_2$OH | H | |
| 75 | (tetrazole: N—N / N—N—H) | H | n-propyl | OCH$_2$ | 6-Cl | H | |
| 76 | NHSO$_2$CF$_3$ | H | n-butyl | O | 6-CH$_2$OH | H | |

Utility

The hormone angiotensin II (AII) produces numerous biological responses (e.g. vasoconstriction) through stimulation of its receptors on cell membranes. For the purpose of identifying compounds such as AII antagonists which are capable of interacting with the AII receptor, a ligand-receptor binding assay was utilized for the initial screen. The assay was carried out according to the method described by [Glossmann et al., J. Biol. Chem., 249, 825 (1974)], but with some modifications. The reaction mixture contained rat adrenal cortical microsomes (source of AII receptor) in Tris buffer and 2 nM of $^3$H-AII with or without potential AII antagonist. This mixture was incubated for 1 hour at room temperature and the reaction was subsequently terminated by rapid filtration and rinsing through glass microfibre filter. Receptor-bound $^3$H-AII trapped in filter was quantitated by scintillation counting. The inhibitory concentration (IC$_{50}$) of potential AII antagonist which gives 50% displacement of the total specifically bound $^3$H-AII is presented as a measure of the affinity of such compound for the AII receptor (see Table 4).

The potential antihypertensive effects of the compounds of this invention may be demonstrated by administering the compounds to rats made hypertensive by ligation of the left renal artery [Cagniano et al., J. Pharmacol. Exp. Ther., 208, 310 (1979)]. This procedure increases blood pressure by increasing renin production with consequent elevation of AII levels. Compounds are administered orally and/or intravenously via a cannula in the jugular vein. Arterial blood pressure is continuously measured directly through a cartoid artery cannula and recorded using a pressure transducer and a polygraph. Blood pressure levels after treatment are compared to pretreatment levels to determine the antihypertensive effects of the compounds (See Table 4).

TABLE 4

| Ex. No. | Angiotensin II Receptor Binding IC$_{50}$ μ molar | Antihypertensive Effects in Renal Hypertensive Rats | |
|---|---|---|---|
| | | Intravenous Activity[1] | Oral Activity[2] |
| 1 | 8.3 | NA | NA |
| 2 | 2.1 | NA | NA |
| 3 | 4.4 | NT | NT |
| 4 | 15 | NT | NT |
| 5 | 29 | NT | NT |
| 6 | 2.8 | NT | NA |
| 27 | 0.22 | + | + |
| 28 | 0.37 | + | NA |
| 29 | 0.92 | + | NA |
| 30 | 1.0 | + | NA |
| 31 | 1.4 | + | NA |
| 32 | 0.5 | + | NA |
| 33 | 5 | + | + |
| 34 | 6.3 | + | NA |
| 35 | 21 | + | NA |
| 36 | 2.5 | + | NA |
| 37 | 5.7 | + | NA |
| 38 | 11 | + | NA |

[1]Significant decrease in blood pressure at 10 mg/kg or less.
[2]Significant decrease in blood pressure at 100 mg/kg or less.
NA - Not active at dosage administered. Although many of the compounds tested were not active orally, they were active intravenously. Although the compounds of Examples 1 and 2 did not exhibit activity either orally or intravenously at the dosages tested, it is expected that they would exhibit intravenous activity at higher doses because they exhibit ability to bind Angiotensin II receptor.
NT - Not tested.

Dosage Forms

The compounds of this invention can be administered for the treatment of hypertension according to the invention by any means that effects contact of the active ingredient compound with the site of action in the body of a warm-blooded animal. For example, administration can be parenteral, i.e., subcutaneous, intravenous, intramuscular, or intraperitoneal. Alternatively, or concurrently, in some cases administration can be by the oral route.

The compounds can be administered by any conventional means available for use in conjunction with pharmaceuticals, either as individual therapeutic agents or in a combination of therapeutic agents. Diuretics such as furosemide and hydrochlorothiazide may enhance the antihypertensive effect of the benzimidazoles of this invention when the drugs are administered in physical combination or when the diuretic is administered before the benzimidazole. The benzimidazoles can be used in conjunction with non-steroidal anti-inflammatory drugs (NSAID's) such as ibuprofen and indomethacin to prevent the renal faialure that sometimes occurs upon administration of NSAID. Other NSAID's which can be administered in conjunction with the benzimidazoles include piroxicam, naproxen, ketoprofen, tolmetin meclofenamate, sulindac and azapropazone. The benzimidazoles can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.5 to 500 milligrams per kilogram of body weight. Ordinarily, from 1 to 100, and preferably 2 to 80, milligrams per kilogram per day in one or more applications is effective to obtain desired results.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl or propylparaben, and chlorobutanol.

Suitable pharmaceutical carriers are described in Remington's Pharmaceutical Sciences, A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

We claim:

1. A compound of the formula

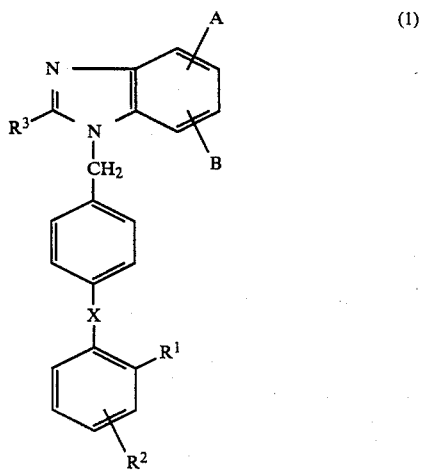

where
$R^1$ is $-CO_2H$, $-NHSO_2CF_3$, or 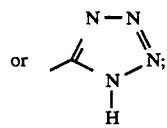

$R^2$ is H, halogen, $NO_2$, methoxy, or alkyl of 1 to 4 carbon atoms;

$R^3$ is alkyl of 1 to 6 carbon atoms, alkenyl or alkynyl of 3 to 6 carbon atoms each of which may be unsubstituted or substituted with a halogen atom, —$OR^4$ or up to two —$CO_2R^4$; with the proviso that when $R^3$ is methyl it must be substituted with —$OR^4$ or —$CO_2R^4$;

$R^4$ is H, or alkyl of 1–4 carbon atoms;

$R^5$ is H, alkyl of 1 to 5 carbon atoms, cycoalkyl of 3 to 6 carbon atoms, $(CH_2)_mC_6H_5$, $OR^6$, or $NR^7R^8$;

$R^6$ H, alkyl of 1 to 5 carbon atoms, cycloalkyl of 3 to 6 carbon atoms or phenyl;

$R^7$ and $R^8$ independently are H, alkyl of 1 to 4 carbon atoms, phenyl, benzyl or taken together with nitrogen form a ring of the formula

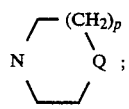

Q is $NR^9$, O, or $CH_2$;

$R^9$ is H, alkyl of 1 to 4 carbon atoms, or phenyl;

$R^{10}$ is alkyl of 1 to 6 carbon atoms;

A is H, alkyl of 1 to 10 carbon atoms, $C_rF_{2r+1}$ where r=1–6, $C_6F_5$, halogen, alkoxy of 1 to 6 carbon atoms;

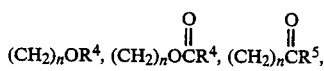

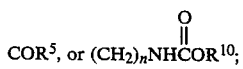

B is H, alkyl of 1 to 10 carbon atoms, $C_rF_{2r+1}$ where r=1–6, $C_6F_5$, halogen or alkoxy of 1 to 6 carbon atoms;

X is a carbon-carbon single bond, —CO—, —O—, —NHCO—, or —$OCH_2$—; n is 1 to 6;

m is 0 to 3;

p is 0 or 1;

or a pharmaceutically acceptable salt thereof; provided that:

(1) when $R^3$ is methyl is must be substituted with —$OR^4$ or $CO_2R^4$;

(2) when $R^3$ is —CH=CH—$CO_2$Et, then X is not —NHCO;

(3) when $R^3$ is $CH_2OH$, CH=$CHCO_2H$ or $CH_2CH_2CO_2H$ and A and B are hydrogen, then X cannot be a carbon-carbon single bond;

(4) when $R^1$ is —$CO_2H$, $R^3$ is butyl, and X is a carbon-carbon single bond, then A is not 5-Cl;

(5) when $R^1$ is —$CO_2H$, $R^3$ is $CH_2OCH_3$ and X is a carbon-carbon single bond, then A is not 5-$CH_2OH$;

(6) when $R^1$ is —$CO_2H$, X is not —O—.

2. Compound of claim 1 wherein
$R^1$ is —$CO_2H$, —$NHSO_2CF_3$; or

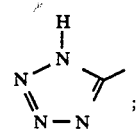

$R^2$ is hydrogen;

$R^3$ is alkyl of 3 to 6 carbon atoms, alkenyl or alkynyl of 3 to 6 carbon atoms each of which may be unsubstituted or substituted with —$OR^4$ or $CO_2R^4$;

$R^5$ is H, alkyl of 1 to 5 carbon atoms, $OR^6$ or $NR^7R^8$;

$R^6$ is H, alkyl of 1 to 5 carbon atoms;

A is halogen, alkoxy of 1 to 6 carbon atoms;

B is H; or a pharmaceutically acceptable salt thereof.

3. Compound of claim 2 wherein $R^3$ is alkyl of 3 to 5 carbon atoms, alkenyl or akynyl of 3 to 5 carbon atoms each of which may be unsubstituted or substituted with OH, $OCH_3$, $CO_2H$ or $CO_2CH_3$;

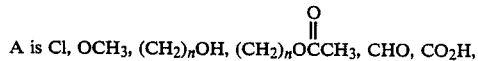

A is Cl, $OCH_3$, $(CH_2)_nOH$, $(CH_2)_nOCCH_3$, CHO, $CO_2H$,

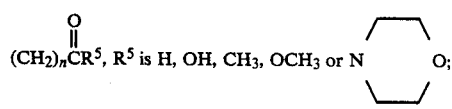

n is 1–2;

X is a carbon-carbon single bond, or —NHCO—; or a pharmaceutically acceptable salt thereof.

4. Compound of claim 1 which is 2-butyl-1[(2'-carboxybiphenyl-4-yl)methyl]-6-hydroxymethyl-benzimidazole, or a pharmaceutically suitable salt thereof.

5. Compound of claim 1 which is 2-butyl-1-[(2'-carboxybiphenyl-4-yl)methyl]-5-hydroxymethyl-benzimidazole, or a pharmaceutically suitable salt thereof.

6. Compound of claim 1 which is 2-butyl-1-[2'-carboxybiphenyl-4-yl)methyl]-6-methoxybenzimidazole, or a pharmaceutically suitable salt thereof.

7. Compound of claim 1 which is 2-(1-butenyl)-1[(2'-carboxybiphenyl-4-yl)-methyl]-6-hydroxymethylbenzimidazole, or a pharmaceutically suitable salt thereof.

8. Compound of claim 1 which is 2-butyl-1-[(2'-carboxybiphenyl-4-yl)methyl]-6-chlorobenzimidazole, or a pharmaceutically suitable salt thereof.

9. Pharmaceutical composition useful for treating hypertension or congestive heart failure in a warm-blooded animal comprising a suitable pharmaceutical carrier and a compound of any one of claims 1 through 8 in an amount effective to lower the animal's blood pressure or relieve the congestion.

10. Method of treating hypertension in a warm-blooded animal comprising administering to the animal in an amount effective to lower the animal's blood pressure a compound of any one of claims 1 through 8.

11. Method of treating congestive heart failure in a warm-blooded animal comprising administering to the animal a compound of any one of claims 1 through 8 in an amount effective to correct the hemodynamic burden on the heart to relieve the congestion.

12. Method of treating hypertension in a warm-blooded animal comprising administering to the animal in an amount effective to lower the animal's blood pressure a compound of the formula:

(1)

where
$R^1$ is —$CO_2H$, —$NHSO_2CF_3$, or $R^2$ is H, halogen, $NO_2$, methoxy, or alkyl of 1 to 4 carbon atoms;

$R^3$ is alkyl of 1 to 6 carbon atoms, alkenyl or alkynyl of 3 to 6 carbon atoms each of which may be unsubstituted or substituted with a halogen atom, —$OR^4$ or up to two —$CO_2R^4$; with the proviso that when $R^3$ is methyl it must be substituted with —$OR^4$ or —$CO_2R^4$;

$R^4$ is H, or alkyl of 1–4 carbon atoms;

$R^5$ is H, alkyl of 1 to 5 carbon atoms, cycloalkyl of 3 to 6 carbon atoms, $(CH_2)_mC_6H_5$, $OR^6$, or $NR^7R^8$;

$R^6$ is H, alkyl of 1 to 5 carbon atoms, cycloalkyl of 3 to 6 carbon atoms or phenyl;

$R^7$ and $R^8$ independently are H, alkyl of 1 to 4 carbon atoms, phenyl, benzyl or taken together with nitrogen form a ring of the formula Q is $NR^9$, O, or $CH_2$;
$R^9$ is H, alkyl of 1 to 4 carbon atoms, or phenyl;
$R^{10}$ is alkyl of 1 to 6 carbon atoms;
A is H, alkyl of 1 to 10 carbon atoms, $C_rF_{2r+1}$ where $r=1-6$, $C_6F_5$, halogen, alkoxy of 1 to 6 carbon atoms;

$(CH_2)_nOR^4$, $(CH_2)_nOCR^4$, $(CH_2)_nCR^5$, $COR^5$, or $(CH_2)_nNHCR^{10}$;

B is H, alkyl of 1 to 10 carbon atoms, $C_rF_{2r+1}$ where $r=1-6$, $C_6F_5$, halogen or alkoxy of 1 to 6 carbon atoms;

X is a carbon-carbon single bond, —CO—, —O—, —NHCO—, or —$OCH_2$—;

n is 1 to 6;
m is 0 to 3;
p is 0 or 1;
or a pharmaceutically acceptable salt thereof;
provided that:

(1) when $R^3$ is methyl it must be substituted with —$OR^4$ or —$CO_2R^4$;

(2) when $R^3$ is —CH=CH—$CO_2Et$, then X is not —NHCO;

(3) when $R^3$ is $CH_2OH$, CH=CHCO$_2$H or $CH_2CH_2CO_2H$ and A and B are hydrogen, then X cannot be a carbon-carbon single bond;

(4) when $R^1$ is —$CO_2H$, $R^3$ is butyl, and X is a carbon-carbon single bond, then A is not 5-Cl;

(5) when $R^1$ is —$CO_2H$, $R^3$ is $CH_2OCH_3$ and X is a carbon-carbon single bond, then A is not 5-$CH_2OH$.

13. Method of treating congestive heart failure in warm-blooded animals comprising administering to the animal a compound of the formula:

(1)

where
$R^1$ is —$CO_2H$, —$NHSO_2CF_3$, or $R^2$ is H, halogen, $NO_2$, methoxy, or alkyl of 1 to 4 carbon atoms;

$R^3$ is alkyl of 1 to 6 carbon atoms, alkenyl or alkynyl of 3 to 6 carbon atoms each of which may be unsubstituted or substituted with a halogen atom, —$OR^4$ or up to two —$CO_2R^4$; with the proviso that when $R^3$ is methyl it must be substituted with —$OR^4$ or —$CO_2R^4$;

$R^4$ is H, or alkyl of 1–4 carbon atoms;

$R^5$ is H, alkyl of 1 to 5 carbon atoms, cycloalkyl of 3 to 6 carbon atoms, $(CH_2)_m C_6H_5$, $OR^6$, or $NR^7R^8$;

$R^6$ H, alkyl of 1 to 5 carbon atoms, cycloalkyl of 3 to 6 carbon atoms or phenyl;

$R^7$ and $R^8$ independently are H, alkyl of 1 to 4 carbon atoms, phenyl, benzyl or taken together with nitrogen form a ring of the formula

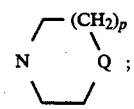

Q is $NR^9$, O, or $CH_2$;

$R^9$ is H, alkyl of 1 to 4 carbon atoms, or phenyl;

$R^{10}$ is alkyl of 1 to 6 carbon atoms;

A is H, alkyl of 1 to 10 carbon atoms, $C_rF_{2r+1}$ where r=1–6, $C_6F_5$, halogen, alkoxy of 1 to 6 carbon atoms;

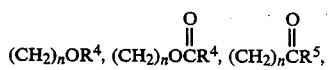

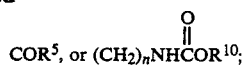

B is H, alkyl of 1 to 10 carbon atoms, $C_rF_{2r+1}$ where r=1–6, $C_6F_5$, halogen or alkoxy of 1 to 6 carbon atoms;

X is a carbon-carbon single bond, —CO—, —O—, —NHCO—, or —OCH$_2$—;

n is 1 to 6;

m is 0 to 3;

p is 0 or 1;

or a pharmaceutically acceptable salt thereof in an amount effective to correct the hemodynamic burden on the heart to relieve the congestion;

provided that:
(1) when $R^3$ is methyl it must be substituted with —$OR^4$ or —$CO_2R^4$;
(2) when $R^3$ is —CH=CH—CO$_2$Et, then X is not —NHCO;
(3) when $R^3$ is CH$_2$OH, CH=CHCO$_2$H or CH$_2$CH$_2$CO$_2$H and A and B are hydrogen, then X cannot be a carbon-carbon single bond;
(4) when $R^1$ is —CO$_2$H, $R^3$ is butyl, and X is a carbon-carbon single bond, then A is not 5-Cl;
(5) when $R^1$ is —CO$_2$H, $R^3$ is CH$_2$OCH$_3$ and X is a carbon-carbon single bond, then A is not 5-CH$_2$OH.

* * * * *